US010638993B2

(12) United States Patent
Yun et al.

(10) Patent No.: US 10,638,993 B2
(45) Date of Patent: May 5, 2020

(54) COMPUTED TOMOGRAPHY APPARATUS AND CONTROL METHOD FOR THE SAME

(71) Applicant: Samsung Electronics Co., Ltd, Gyeonggi-do (KR)

(72) Inventors: Seung Man Yun, Gyeonggi-do (KR); Rifu Toshihiro, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 566 days.

(21) Appl. No.: 15/361,322

(22) Filed: Nov. 25, 2016

(65) Prior Publication Data

US 2017/0143292 A1 May 25, 2017

(30) Foreign Application Priority Data

Nov. 25, 2015 (KR) .................. 10-2015-0165164

(51) Int. Cl.
*A61B 6/00* (2006.01)
*G06T 1/00* (2006.01)
(Continued)

(52) U.S. Cl.
CPC .............. *A61B 6/488* (2013.01); *A61B 6/465* (2013.01); *A61B 6/466* (2013.01); *A61B 6/467* (2013.01);
(Continued)

(58) Field of Classification Search
CPC ......... A61B 6/032; A61B 6/456; A61B 6/466; A61B 6/467; A61B 6/48; A61B 6/488; A61B 6/52; A61B 6/5211; A61B 6/5217; A61B 6/5229; A61B 6/5235; A61B 6/5294; A61B 6/54; A61B 6/542; A61B 6/544; A61B 6/58; A61B 2560/00; A61B 2560/02; A61B 2560/0223; A61B 2560/0266; G06T 1/00; G06T 1/0007; G06T 1/0014;
(Continued)

(56) References Cited

U.S. PATENT DOCUMENTS

2005/0008115 A1* 1/2005 Tsukagoshi ............ A61B 6/032
378/4
2006/0115039 A1 6/2006 Gohno
(Continued)

FOREIGN PATENT DOCUMENTS

JP 2004073397 3/2004
JP 2006026417 2/2006
WO 9732630 A1 9/1997

*Primary Examiner* — Anastasia Midkiff

(57) ABSTRACT

A system and method for a Computed Tomography (CT) process for calculating a dose of radiation to which an object is expected to be exposed when performing a CT scan on the object is disclosed. The CT apparatus includes a scanner that performs a scout scan on the object; an image processor that acquires image data for the shape of the object based on a scout scan image, compares the acquired image data to pre-stored image data, and selects an image data having greater similarity than predetermined similarity to the acquired image data from among the pre-stored image data; and a controller that calculates a dose of radiation to which the object is expected to be exposed, based on a dose of radiation corresponding to the selected at least one image data, and performs a CT scan on the object based on the calculated dose of radiation.

18 Claims, 26 Drawing Sheets

(51) Int. Cl.
*G06T 7/00* (2017.01)
*G06T 7/174* (2017.01)
*G01T 7/00* (2006.01)

(52) U.S. Cl.
CPC .......... *A61B 6/5217* (2013.01); *A61B 6/5294* (2013.01); *A61B 6/58* (2013.01); *G01T 7/005* (2013.01); *G06T 1/0014* (2013.01); *G06T 7/0014* (2013.01); *G06T 7/174* (2017.01); *A61B 6/5229* (2013.01); *A61B 6/542* (2013.01); *A61B 2560/0266* (2013.01); *G01N 2223/303* (2013.01); *G01N 2223/304* (2013.01); *G01N 2223/306* (2013.01)

(58) Field of Classification Search
CPC ...................................................... G06T 3/00; G06T 3/0056; G06T 7/00; G06T 7/0012; G06T 7/0014; G06T 7/149; G06T 7/174; G01T 1/16; G01T 1/24; G01T 1/245; G01T 7/005; G01N 2223/30; G01N 2223/303; G01N 2223/304; G01N 2223/306; G01N 2223/426
See application file for complete search history.

(56) References Cited

U.S. PATENT DOCUMENTS

2008/0292055 A1 11/2008 Boone
2014/0185751 A1 7/2014 De Man et al.

\* cited by examiner

| | A | B |
|---|---|---|
| Projection profile Similarity | 70% | 90% |
| Bone Structure Similarity | 85% | 80% |
| Total Similarity | 77.5% | 85% |
| Data about Corresponding Dose of Radiation | 200 | 170 |

CALCULATE APPROPRIATE DOSE OF RADIATION FOR OBJECT

COMPUTED TOMOGRAPHY APPARATUS AND CONTROL METHOD FOR THE SAME

CROSS-REFERENCE TO RELATED APPLICATION(S) AND CLAIM OF PRIORITY

The present application is related to and claims the benefit of Korean Patent Application No. 10-2015-0165164, filed on Nov. 25, 2015 in the Korean Intellectual Property Office, the disclosure of which is incorporated herein by reference.

TECHNICAL FIELD

The present application relates generally to medical imaging, and more particularly to a Computed Tomography (CT) apparatus and a control method for the same.

BACKGROUND

A medical imaging apparatus is equipment for acquiring images about the internal structures of objects. The medical imaging apparatus, which is non-invasive examination equipment, scans structural details, internal tissues, and flows of fluid in the human body, processes the results of the scanning, and then displays the processed images for users. A user such as a doctor examines medical images output from such a medical imaging apparatus to diagnose a patient's health status and disease.

A representative one of medical imaging apparatuses for irradiating X-rays onto a patient to scan the patient is a Computed Tomography (CT) apparatus. The CT apparatus can irradiate X-rays onto an object in different directions, and then reconstruct images using a computer. The CT apparatus can image the internal tissues of an object using a fact that different tissues in the object have different attenuation coefficients obtained by digitizing degrees to which the respective tissues absorb or transmit radiation.

Since the CT apparatus can provide section images of an object, it can represent the internal structures (for example, organs, such as kidney, lungs, etc.) of an object such that they do not overlap with each other compared to a general X-ray imaging apparatus. For this reason, the CT apparatus is widely used for precise diagnosis of diseases.

The CT apparatus performs a CT scan on an object to acquire raw data, and uses the raw data to reconstruct a CT image. The raw data may be projection data acquired by projecting X-rays on the object, or a sinogram, which is a group of such projection data.

Before a CT scan is performed on an object, a pre-shot or a scout scan can be performed with a low dose of X-rays in order to control exposure parameters, such as a tube voltage, tube current, an exposure time, the kind and thickness of a filter, a target material of an anode, a focal spot size, etc., which are to be applied to an X-ray source.

SUMMARY

To address the above-discussed deficiencies, it is a primary object to provide a Computed Tomography (CT) apparatus of acquiring image data for the shape of an object by performing a scout scan on the object, and comparing the image data for the shape of the object to image data stored in database to thereby calculate a dose of radiation to which the object is expected to be exposed when performing a CT scan on the object, and a method of controlling the CT apparatus.

Additional aspects of the disclosure will be set forth in part in the description which follows and, in part, will be obvious from the description, or may be learned by practice of the disclosure.

In accordance with one aspect of the present disclosure, a Computed Tomography (CT) apparatus for performing a CT scan on an object is provided. The CT apparatus includes: a scanner configured to perform a scout scan on the object; a processor configured to acquire image data for the shape of the object based on a scout scan image acquired by the scout scan, to compare the acquired image data to pre-stored image data, and to select at least one image data having greater similarity than predetermined similarity to the acquired image data from among the pre-stored image data and calculate a dose of radiation to which the object is expected to be exposed, based on a dose of radiation corresponding to the selected at least one image data, and to perform a CT scan on the object based on the calculated dose of radiation.

The scanner can perform a scout scan on at least one of a top view of the object and a lateral view of the object.

The image data for the shape of the object can include at least one image data between image data for a top view of the object and image data for a lateral view of the object.

The image data for the shape of the object can include at least one image data among projection profile data of the object, bone structure image data of the object, and contour image data of the object.

The processor acquires the projection profile data of the object, based on at least one of the brightness of the scout scan image and the intensity of image signals of the scout scan image.

The processor performs image processing on the projection profile data of the object to create at least one image data between the bone structure image data of the object and the contour image data of the object.

The processor compares the projection profile data of the object to pre-stored projection profile data.

The processor compares the bone structure image data of the object to pre-stored bone structure image data.

The processor compares the contour image data of the object to pre-stored contour image data.

The processor further acquires image data by performing the CT scan on the object.

The controller further detects a dose of radiation to which the object is exposed, based on the image data acquired by performing the CT scan on the object.

The processor further compares the detected dose of radiation to which the object is exposed, to the dose of radiation to which the object is expected to be exposed to calculate a difference, and corrects the difference to perform a CT scan on the object.

The CT apparatus can include a storage unit configured to store the acquired image data of the object and the detected dose of radiation of the object.

The storage unit stores the difference calculated by comparing the detected dose of radiation to which the object is exposed, to the dose of radiation to which the object is expected to be exposed.

In accordance with another aspect of the present disclosure, a method for controlling a CT apparatus is provided. The method includes: performing a scout scan on an object; acquiring image data for the shape of the object based on a scout scan image obtained by performing the scout scan on the object; comparing the image data to pre-stored image data; selecting at least one image data having greater similarity than predetermined similarity to the acquired image data from among the pre-stored image data; calculating a dose of radiation to which the object is expected to be exposed, based on a dose of radiation corresponding to the selected at least one image data; and performing a CT scan on the object based on the calculated dose of radiation.

The performing of the scout scan on the object can include performing a scout scan on at least one of a top view of the object and a lateral view of the object.

The acquiring of the image data for the shape of the object can include acquiring at least one data among projection profile data of the object, bone structure image data of the object, and contour image data of the object.

The acquiring of the image data for the shape of the object can include acquiring the projection profile data of the object, based on at least one of the brightness of the scout scan image and the intensity of image signals of the scout scan image.

The acquiring of the image data for the shape of the object can include performing image processing on the projection profile data of the object to create at least one data between the bone structure image data of the object and the contour image data of the object.

The comparing of the acquired image data to the pre-stored image data can include comparing the acquired projection profile data of the object to pre-stored projection profile data.

The comparing of the acquired image data to the pre-stored image data can include comparing the acquired bone structure image data of the object to pre-stored bone structure image data.

The comparing of the acquired image data to the pre-stored image data can include comparing the acquired contour image data of the object to pre-stored contour image data.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
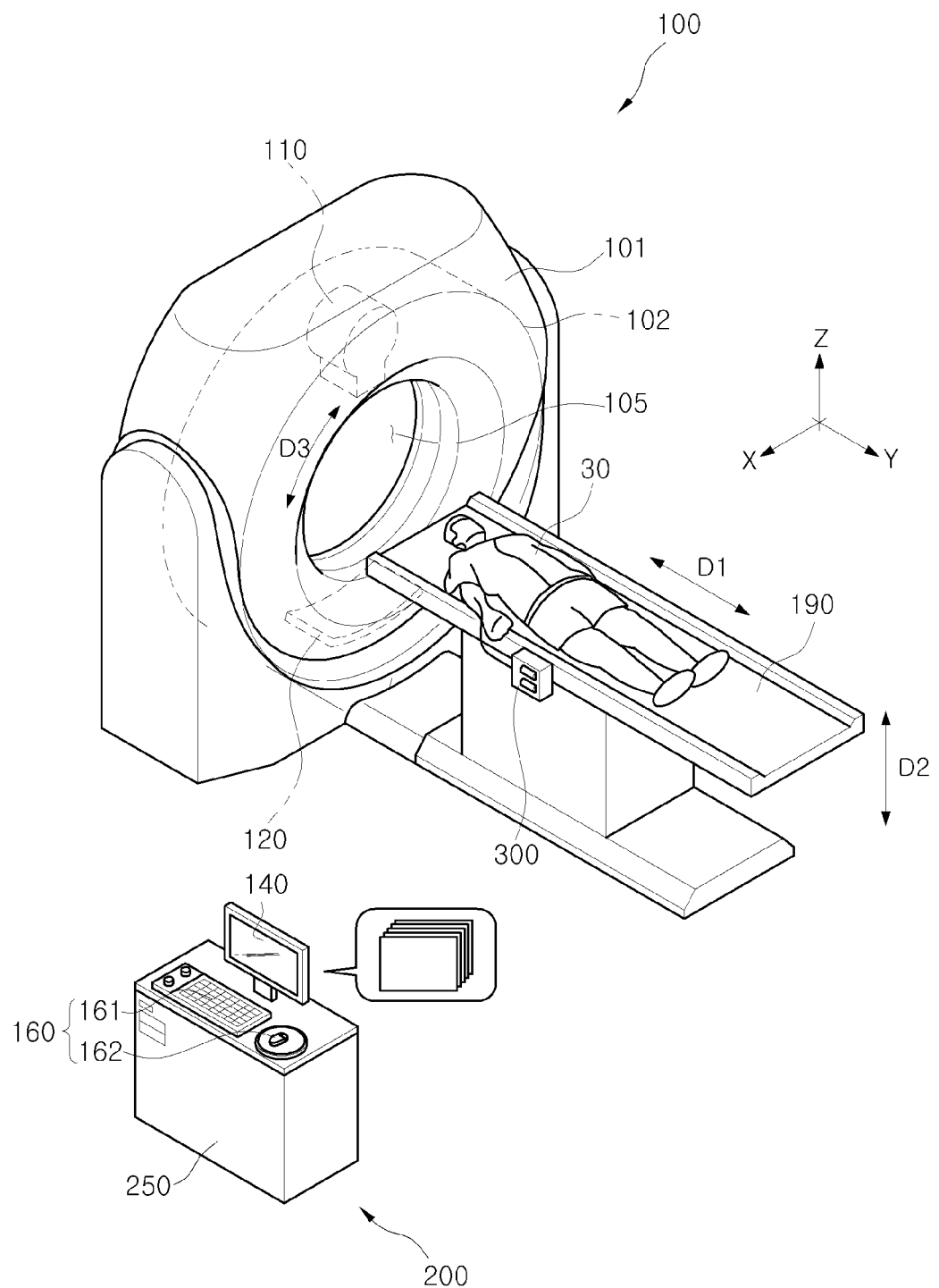
FIG. 1 illustrates a perspective view showing the outer appearance of a CT apparatus according to an embodiment of the present disclosure.

FIGS. 1 through 19B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged imaging system.

Advantages and features of the present disclosure and a method of achieving the advantages and features will be apparent by referring to embodiments described below in connection with the accompanying drawings. However, the present disclosure is not restricted by these embodiments but can be implemented in many different forms. The present embodiments are provided to complete the disclosure of the present invention and to allow those having ordinary skill in the art to understand the scope of the present disclosure. The present disclosure is defined by the category of the claims. Like reference numerals refer to like elements throughout this specification.

Terms used in this specification will be briefly described, and the present disclosure will be described in detail.

Although general terms being widely used at the present disclosure were selected as terminology used in the present disclosure while considering the functions of the present disclosure, they may vary according to intentions of one of ordinary skill in the art, judicial precedents, the advent of new technologies, and the like. Terms arbitrarily selected by the applicant of the present disclosure may also be used in a specific case. In this case, their meanings need to be given in the detailed description of the present disclosure. Hence, the terms must be defined based on the meanings of the terms and the contents of the entire specification, not by simply stating the terms themselves.

It will be understood that when the terms "includes," "comprises," "including," and/or "comprising," when used in this specification, specify the presence of stated elements and/or components, but do not preclude the presence or addition of one or more elements and/or components thereof. As used herein, the terms "part", "module", or "unit" refers to a unit that can perform at least one function or operation, and may be implemented as a software or hardware component such as a Field Programmable Gate Array (FPGA) or an Application Specific Integrated Circuit (ASIC). However, the term "part", "module" or "unit" is not limited to software or hardware. The "part", "module", or "unit" may be configured in an addressable storage medium, or may be configured to run on at least one processor. Therefore, as an example, the "part", "module", or "unit" includes: components such as software components, object-oriented software components, class components, and task components; processors, functions, attributes, procedures, sub-routines, segments of program codes, drivers, firmware, microcodes, circuits, data, databases, data structures, tables, arrays, and variables. Functions provided in the components and the "part", "module", or "unit" may be integrated into the smaller number of components and the "part", "module", or "unit", or may be sub-divided into additional components and an additional "part", "module", or "unit".

Hereinafter, embodiments of the present disclosure will be described in detail with reference to the accompanying drawings so that the present disclosure may be readily implemented by those skilled in the art. However, the present disclosure can be implemented in different forms, and is not limited to the embodiments which will be described below. In the drawings, parts irrelevant to the description are omitted for the simplicity of explanation.

In this specification, the term "image" can mean multi-dimensional data configured with discrete image elements (for example, pixels in a 2Dimensional (2D) image and voxels in a 3Dimensional (3D) image). For example, an image can include a medical image of an object, acquired by a Computed Tomography (CT) apparatus.

In this specification, the term "CT image" can mean a combined image of a plurality of X-ray images acquired by scanning an object through a scanner rotating around the object with respect to at least one axis for the object.

In this specification, the term "object" may be a human, an animal, or the entire or a part of a human or an animal. For example, the object can include at least one of an organ, such as the liver, heart, uterus, brain, breasts, abdomen, etc., and blood vessels. Also, the term "object" may be a phantom. The phantom means a material having a volume that is very close to the density and effective atomic number of a living thing, and can include a spherical phantom having similar properties to the human body.

In this specification, the term "user" can be a medical specialist including a doctor, a nurse, a medical technologist, and a radiological technologist, and may also be an engineer who repairs medical equipment. However, the user is not limited to the above-mentioned persons.

Since a CT system can provide section images of an object, it can represent the internal structures (for example, organs, such as kidney, lungs, etc.) of an object such that they do not overlap with each other compared to a general X-ray imaging apparatus.

More specifically, the CT system can include all kinds of CT scanners, such as a Computed Tomography (CT) apparatus, an Optical Coherence Tomography (OCT) apparatus, or a Positron Emission Tomography (PET)-CT apparatus.

In the following description, the CT system is assumed to be a CT apparatus.

The CT system can provide relatively accurate section images of an object by acquiring image data corresponding to a thickness of 2 mm or less several hundreds of times per second and processing the acquired image data. Typically, the CT system had a problem that it could represent only the traverse sections of objects; however, the problem has been overcome with the introduction of various image reconstruction methods as follows. There are 3D image reconstruction methods as follows.

Shade Surface Display (SSD): initial 3D imaging scheme which represents only voxels having constant HU values.

Maximum Intensity Projection (MIP)/Minimum Intensity Projection (MinIP): 3D imaging scheme that represents only ones having the greatest or smallest HU values among voxels constructing an image.

Volume Rendering (VR): scheme for adjusting the colors and transmittances of voxels constructing an image for each region-of-interest.

Virtual Endoscopy (VE): scheme for enabling endoscopy observation of a 3D image constructed with the VR or SSD scheme.

Multi Planar Reformation (MPR): imaging scheme for reconstruction to other section images, which can reconstruct images freely in a user's desired directions.

Editing: various schemes for arranging peripheral voxels to offer easy observation of a region-of-interest in VR.

Voxel of Interest (VOI): scheme for representing only a selected region in VR.

Hereinafter, a CT apparatus according to an embodiment of the present disclosure will be described with reference to the accompanying drawings, wherein the CT apparatus can include various kinds of apparatuses.

Also, the CT apparatus can be an imaging apparatus requiring a scout scan or a pre-shot.

FIG. 1 illustrates a perspective view showing the outer appearance of a CT apparatus according to an embodiment of the present disclosure.

As shown in FIG. 1, a CT apparatus 100 includes a housing 101 to irradiate and detect X-rays, a table 190 to move an object, and a main body 250 to control operations of the CT apparatus 100.

In the inside of the housing 101, a gantry 102 can be installed in the shape of a cylinder. In the inside of the gantry 102, an X-ray source 110 to irradiate X-rays is disposed to face an X-ray detector 120 to detect X-rays. Hereinafter, the X-ray source 110 and the X-ray detector 120 will be collectively referred to as a scanner.

The X-ray source 110 generates X-rays, and irradiates the X-rays onto an object 30. The X-ray source 110 can be provided as an X-ray source assembly including a filter for filtering X-rays to be irradiated. Herein, the object 30 may be the living body of a human or an animal, or tissues in a living body, such as vessels, bones, muscle, etc., although not limited to these. That is, the object 30 can be anything whose internal structure can be imaged by the CT apparatus 100.

The X-ray detector 120 detects X-rays transmitted through the object 30, and can be opposite to the X-ray source 110. If the table 190 moves so that the object 30 is positioned between the X-ray source 110 and the X-ray detector 120, X-rays irradiated from the X-ray source 110 can be transmitted through the object 30 and then detected by the X-ray detector 120.

The gantry 102 can rotate at an angle of 180 degrees to 360 degrees around a bore 105. If the gantry 102 rotates, the X-ray source 110 and the X-ray detector 120 may also rotate accordingly.

The table 190 conveys the object 30 to be X-ray scanned to the inside of the bore 105. The table 190 can move in a y-axis direction and in a z-axis direction, while maintaining its flat position with respect to the ground. Herein, a direction in which the table 190 moves on the y-axis is defined as a D1 direction, and a direction in which the table 190 moves on the z-axis is defined as a D2 direction. The table 190 can move in the D1 direction and in the D2 direction so that a diagnosis region to be scanned is located between the X-ray source 110 and the X-ray detector 120. The table 190 may be fixed in an x-axis direction, or may be movable in the x-axis direction in the bore 105 in order to adjust the horizontal spacing.

In certain embodiments, in one side of the table 190, a drug injector 300 is installed. The drug injector 300 can be filled with a contrast medium, and connected to the object 30 so that the contrast medium can be injected into the inside of the object 30. The drug injector 300 can be removably provided in the one side of the table 190. Also, unlike FIG. 1, the drug injector 300 can be provided in a separate movable supporter (not shown), instead of one side of the table 190, and can move according to the movement of the supporter.

The main body 250 can accommodate main components (for example, a controller 130 (see FIG. 7)) of the CT apparatus 100. The controller 130 generates various control signals for operations of the CT apparatus 100, such as controlling the rotation of the gantry 102 or the movement of the table 190, or controlling a dose of X-rays irradiated from the X-ray source 110. The controller 130 will be described in detail, herein below.

On the top of the main body 250, a user interface 200 for user manipulations may be mounted. The user interface 200 receives instructions or commands for controlling operations of the CT apparatus 100 from a user, and provides various screens related to operations of the CT apparatus 100. Herein, the user may be a person who diagnoses the object 30 using the CT apparatus 100. For example, the user can be a medical staff including a doctor, a radiologist, and a nurse. However, the user is not limited to such a medical staff, and can be anyone using the CT apparatus 100.

The user interface 200 can include a keyboard 161 and a mouse 162 for receiving the user's inputs. The user interface 200 can further include a hardware input unit, such as a trackball, a foot switch, and a foot pedal, in addition to the keyboard 161 and the mouse 162. The user interface 200 can be mounted on the top of the main body 250, as shown in FIG. 1; however, if the user interface 200 is implemented as a foot switch or a foot pedal, the user interface 200 may be located in the lower portion of the main body 250.

The user interface 200 can include a Graphic User Interface (GUI) such as a touch pad for the user's inputs, that is, the user interface 200 can include a software input unit. If the user interface 200 is implemented in software, the user interface 200 may be displayed through a display 140 which will be described herein below.

As described above, the user interface 200 can include various input units, and the user can input, through the user interface 200, a command for starting X-ray scanning, a command for selecting the kind of scanning, a command for setting a Region-Of-Interest (ROI), a command for selecting a part to be diagnosed, a command for selecting a time at which a contrast medium is injected, a command for selecting a peak point of a contract medium, etc. A command received by the user interface 200 can be transmitted to the main body 250 through wired or wireless communication.

The user interface 200 can include the display 140 to provide various screens for operations of the CT apparatus 100. The display 140 can be a Cathode Ray Tube (CRT) display, a Liquid Crystal Display (LCD), or a Light Emitting Diode (LED) display, although not limited to these.

The display 140 of the user interface 200 can be integrated into a touch pad such as a Touch Screen Panel (TSP) for receiving a user's manipulation commands.

The user interface 200 can display screens related to operation information of the CT apparatus 100, such as a screen for enabling the user to set a ROI, a screen for enabling the user to select a part to be diagnosed, a screen for enabling the user to select a time at which a contrast medium is injected, a screen for enabling the user to select a peak point of a contrast medium, etc., and also display X-ray images acquired through X-ray scanning, through the display 140 implemented as one of various types of displays.

X-ray scanning performed by the CT apparatus 100 may correspond to tomography, and an X-ray image acquired through X-ray scanning may be a single section image, a plurality of section images, or a 3Dimensional (3D) image or a 3D stereo image created based on a plurality of section images, according to the kind of the X-ray scanning. The 3D image means an image obtained by volume-rendering 3D volume data created based on a plurality of section images with respect to a predetermined viewpoint. That is, the 3D image means a 2D projected image obtained by projecting volume data on a 2D plane with respect to a predetermined viewpoint. The 3D stereo image means an image obtained by combining left and right images acquired by volume-rendering volume data with respect to two viewpoints respectively corresponding to a human's left and right eyes.

The user interface 200 can include a plurality of displays 140 to display different kinds of screens, unlike FIG. 1. For example, the user interface 200 can include a first display and a second display, wherein the first display may display a section image, and the second may display a 3D image or a 3D stereo image. According to another example, the first display can display a screen related to operation information of the CT apparatus 100, and the second display can display X-ray images acquired through X-ray scanning.

The above description relates to the CT apparatus 100 (hereinafter, also referred to as a gantry type CT apparatus) including the housing 101 and the gantry 102 in the shape of a cylinder, however, the CT apparatus 100 may have another configuration that is different from the embodiment shown in FIG. 1.

Figure 2:
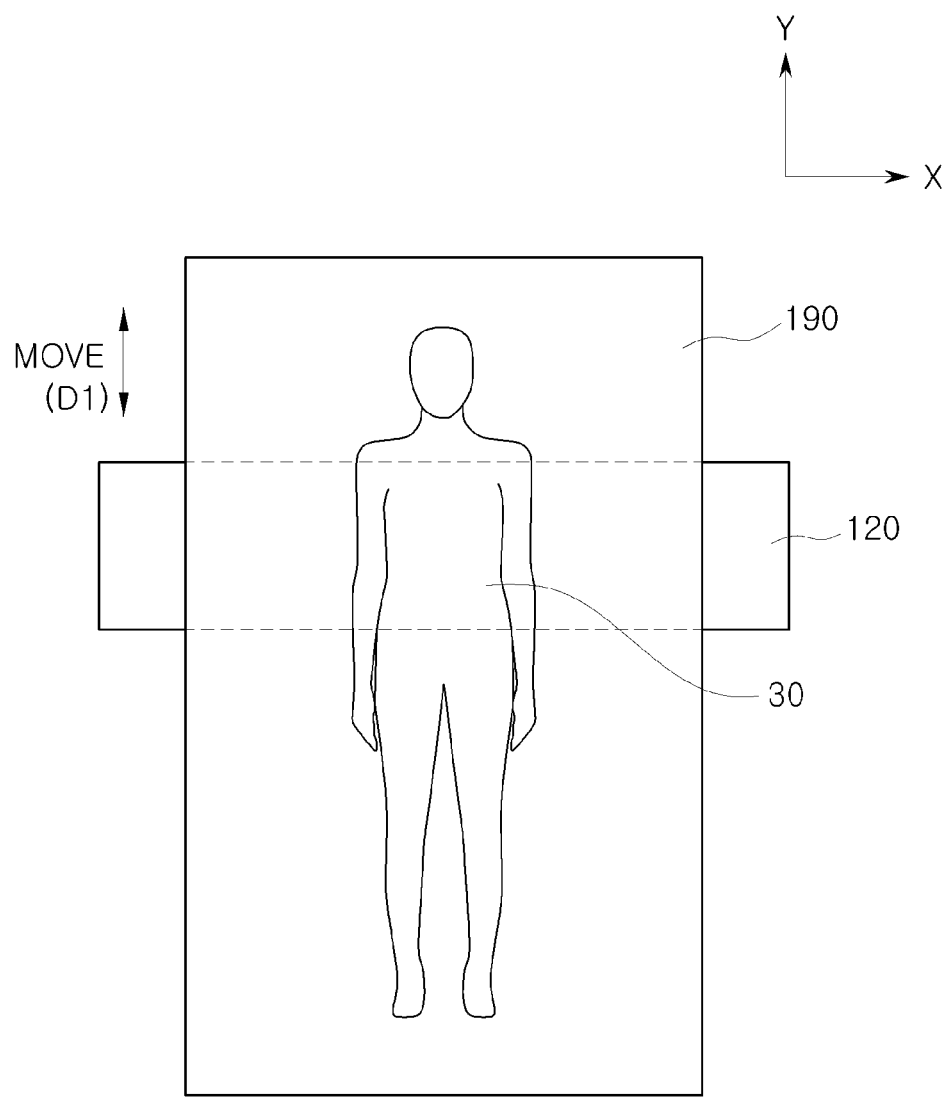
FIG. 2 illustrates a conceptual view for describing operation in which a CT apparatus according to an embodiment of the present disclosure performs a scout scan on an object.
Figure 3:
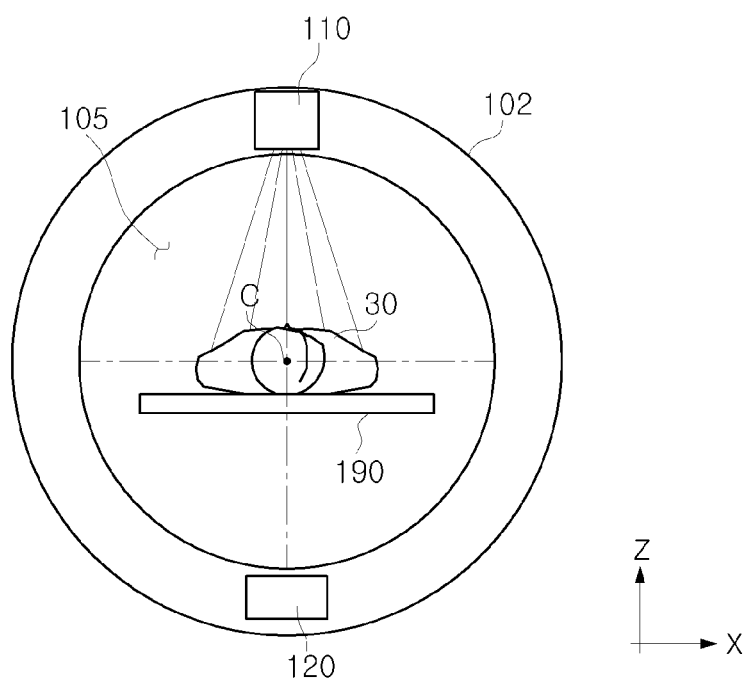
FIG. 3 illustrates a view for describing operation of scanning a top view of an object when performing a scout scan according to an embodiment of the present disclosure.
Figure 4:
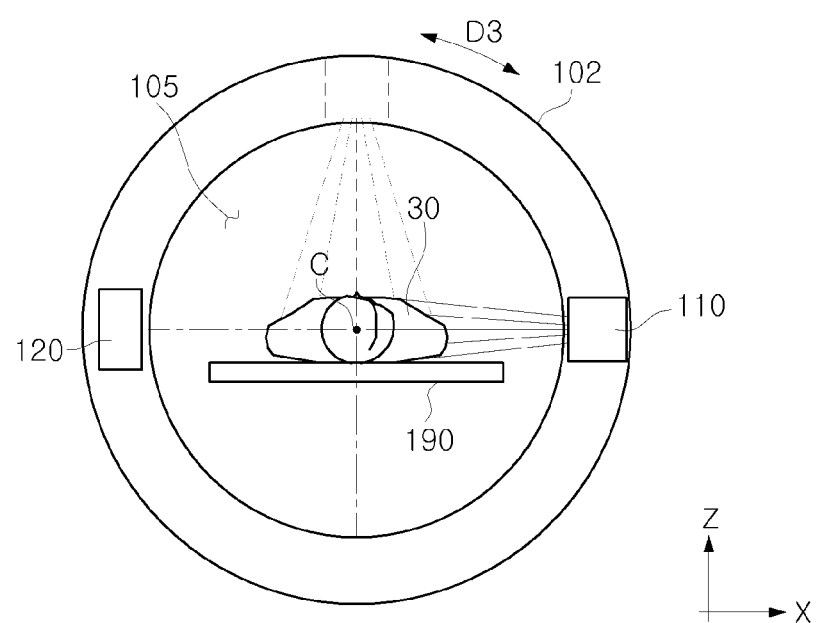
FIG. 4 illustrates a view for describing operation of scanning a lateral view of an object when performing a scout scan according to an embodiment of the present disclosure.

FIG. 2 is a conceptual view for describing operation in which a CT apparatus according to an embodiment of the present disclosure performs a scout scan on an object. FIG. 3 is a view for describing operation of scanning a top view of an object when performing a scout scan according to an embodiment of the present disclosure, and FIG. 4 is a view for describing operation of scanning a lateral view of an object when performing a scout scan according to an embodiment of the present disclosure.

Before a CT scan is performed on the object 30, a scout scan for the object 30 may be performed. The scout scan is also referred to as a scanogram or a topogram.

The scout scan may be to acquire an X-ray scanned image by moving only the table 190 while fixing the gantry 102 without rotating it. That is, the scout scan may be to primarily scan the object 30 before injecting a contrast medium into the object 30.

A user can select a part of the object 30 on which a scout scan is to be performed, through the user interface 200. Accordingly, the table 190 can move in the D1 direction so that the entire body of the object 30 passes between the X-ray source 110 and the X-ray detector 120, and the X-ray source 110 and the X-ray detector 120 can be fixed without rotating to perform X-ray irradiation and detection to thereby perform a scout scan on the entire body of the object 30.

A scout scan image created in this manner can be displayed through the user interface 200, and the user can set a ROI in the scout scan image.

A position of the object 30 at which a CT scan is to be performed and a scanning range of the object 30 on which the CT scan is to be performed can be decided from data of the scout scan image acquired through the scout scan, and parameter values, such as a tube voltage kV, tube current mAs, an exposure time, the kind and thickness of the filter, a target material of the anode, a focal spot size, etc., which are to be applied to the X-ray source 110 also can be decided from the data of the scout scan image.

Also, Tube Current Modulation (TCM) can be decided from the data of the scout scan image, and a dose of radiation to be irradiated from the X-ray source 110 to perform a CT scan on the object 30 can be decided from the data of the scout scan image.

General X-ray imaging technology including the CT apparatus 100 is to measure a degree of attenuation of radiation generated from an X-ray generator when the radiation is transmitted through an object, and to represent the results of the measurement as a digital image. Generally, as the higher dose of radiation is transmitted through an object, the higher quality of X-ray image can be obtained. However, if a high dose of radiation is irradiated onto an object, the object is inevitably exposed to such a high dose of radiation. Accordingly, recently, interest in a CT apparatus using a low dose of radiation is increasing.

A scout scan may be performed before a CT scan is performed on the object 30. According to typical methods, a dose of radiation is calculated using attenuation information of acquired scout image data, or a dose of radiation for scanning an object is predicted according to a measurement value based on an accreditation phantom not considering the actual size of the object.

However, the typical methods have difficulties in predicting an accurate dose of radiation. That is, there is a difference between a predicted dose of radiation and a dose of radiation required when a CT scan is actually performed.

Also, the typical methods could not consider influence by scattered radiation according to the organization of the internal tissues of an object and the size of the object, and operation of predicting a dose of radiation in consideration of such a factor could not be performed quickly before a CT scan starts after a scout scan.

More specifically, the scattered radiation means X-rays scattered when X-rays are irradiated onto an object and then transmitted through or reflected against the object. When a dose of radiation is predicted according to the typical methods, factors of CT Dose Index (CTDI) and Dose Length Product (DLP) were used.

The two factors were used to predict a dose of radiation based on a measurement value with respect to an accreditation phantom. In the case in which a dose of radiation is predicted based on a measurement value with respect to an accreditation phantom, there is a great difference between a measurement value and a dose of radiation to which a patient is exposed when a scan is actually performed, since the patient's actual size is not considered.

The generation cause of the difference is because a dose of radiation due to scattered radiation is not properly reflected to the radiation dose prediction method using the factor CTDI or DLP. The reason is because the scattered radiation depends on the organization, size, etc. of the internal tissue of an object, and the transmission direction or scattering direction of the scattered radiation is irregular.

Also, in the Radiation Theraphy (RT) field, a dose of radiation is predicted according to the Monte Carlo method including predicting a dose of radiation due to scattered radiation; however, the Monte Carlo method also has limitation in predicting a dose of radiation of an object within a short time after a scout scan in the CT field.

In the CT apparatus and a control method thereof according to embodiments of the present disclosure, image data acquired by performing a scout scan on an object may be compared to pre-stored image data, and then a CT scan can be performed using radiation dose prediction data stored in correspondence to the result of the comparison. Accordingly, it is possible to predict a more accurate dose of radiation in consideration of influence by scattered radiation. That is, by using data about a dose of radiation considering influence by scattered radiation, an accurate value about a dose of radiation to which the object 30 is to be actually exposed upon an X-ray scan can be predicted.

That is, since image data for the shape of the object 30 stored in advance in database includes information about influence of scattered radiation, image data for the shape of the object 30 can be compared to the pre-stored data. Also, a dose of scattered radiation can be reflected in real time when a CT scan is performed on the object 30.

Furthermore, after a CT scan is performed on the object 30, data about the influence of scattered radiation may be stored and updated in the database, resulting in an improvement of accuracy in predicting a dose of radiation to which the object 30 is actually exposed when a CT scan is performed on the object 30 later.

Also, a dose of radiation to which the object 30 is exposed, calculated before a CT scan is performed on the object 30 can be compared to a dose of radiation to which the object 30 is actually exposed, calculated after the CT scan is performed on the object 30, to calculate a difference, and the difference can be corrected so that the corrected value is reflected when a CT scan is performed on the object 30 later.

Referring to FIGS. 3 and 4, the table 190 of the CT apparatus 100 can be adjusted in horizontal position or height such that the center of the object 30 matches with the center C of the bore 105, and then moved to the inside of the bore 105. Alternatively, the table 190 of the CT apparatus 100 can move to the inside of the bore 105, and then be adjusted in horizontal position or height such that the center of the object 30 matches with the center C of the bore 105.

In order to perform a scout scan on a top view of the object 30, the X-ray source 110 irradiates, at its position shown in FIG. 3, a low dose of X-rays on the object 30 for a predetermined period or at predetermined time intervals, and the X-ray detector 120 detects X-rays transmitted through the object 30.

Also, in order to perform a scout scan on a lateral view of the object 30, the X-ray source 110 performs a scan at its position shown in FIG. 4.

The CT apparatus 100 rotates the gantry 102 in a D3 direction in order to acquire scout scan image data for the lateral view of the object 30. That is, the X-ray source 110 starts to irradiate X-rays on the top view of the object 30 at its position facing the top view of the object 30, as shown in FIG. 3, and then irradiates X-rays on the lateral view of the object 30 at another position forming 90° with respect to the position at which the X-ray source 110 starts to irradiate X-rays, in correspondence to rotation of the gantry 102, as shown in FIG. 4. FIG. 4 shows a case in which the X-ray source 110 scans the lateral view of the object 30 at its position moved by 90° to the right, however, the X-ray source 110 can scan the lateral view of the object 30 at its position moved by 90° to the left.

Figure 5:
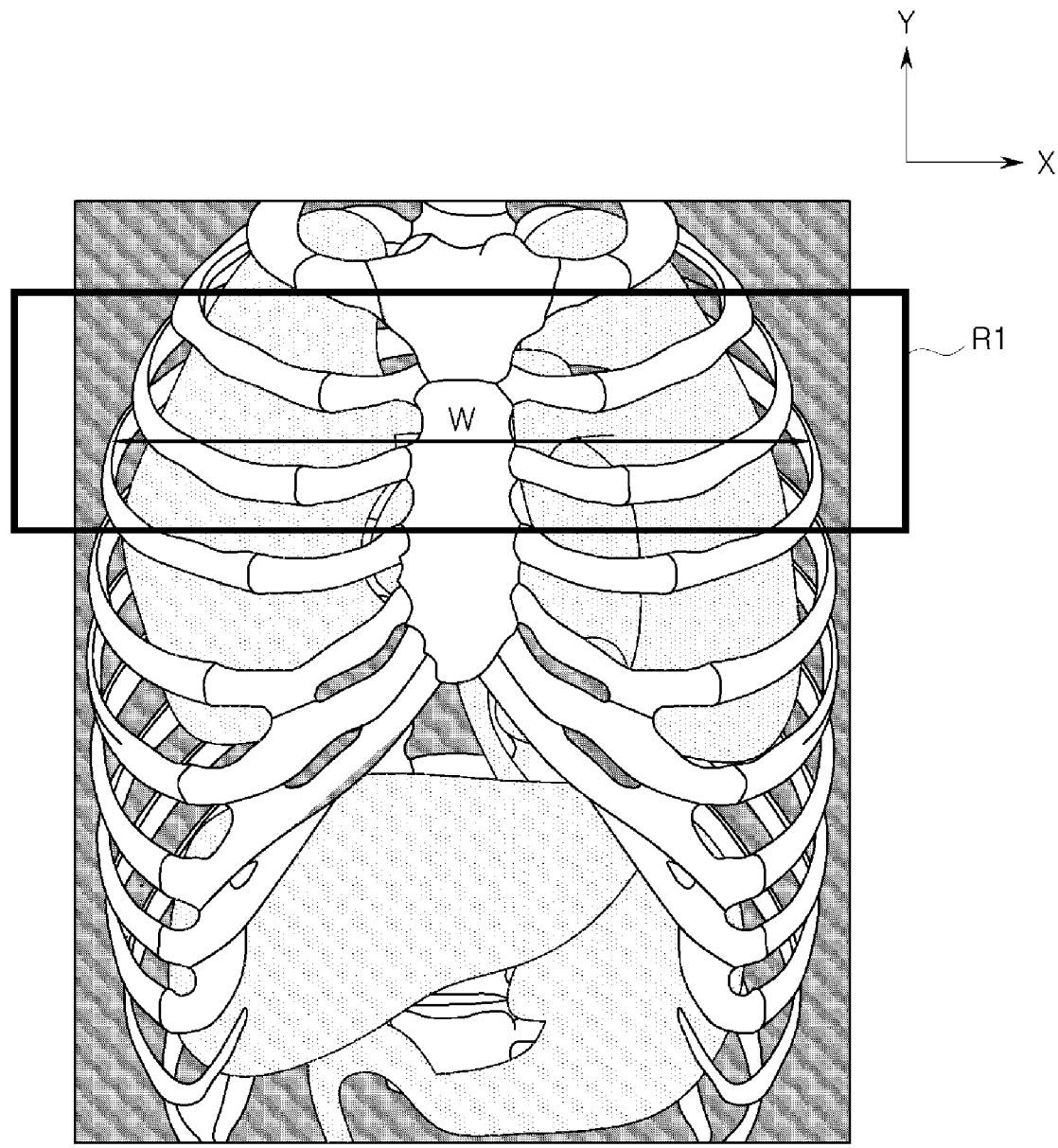
FIG. 5 illustrates image data obtained by performing a scout scan on a top view of an object, according to an embodiment of the present disclosure.
Figure 6:
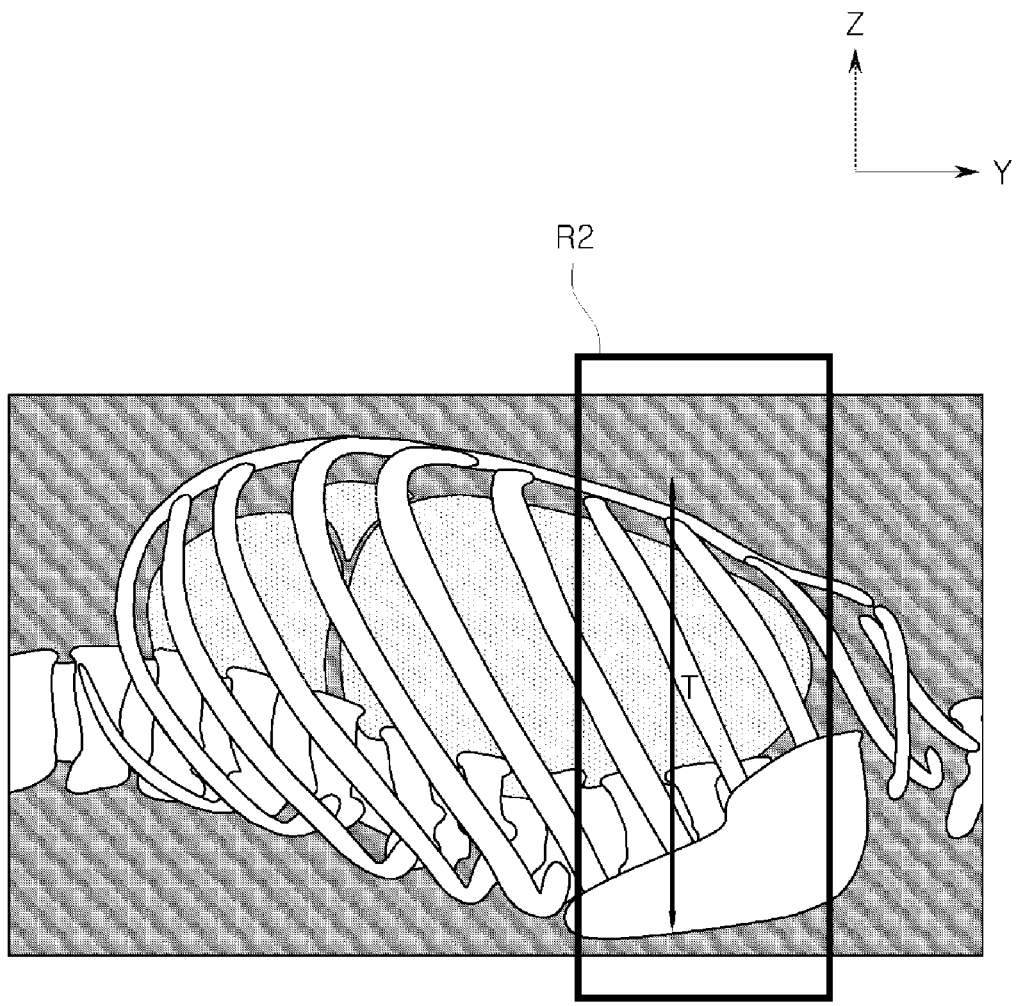
FIG. 6 illustrates image data obtained by performing a scout scan on a lateral view of an object, according to an embodiment of the present disclosure.

FIG. 5 shows image data obtained by performing a scout scan on a top view of an object, according to an embodiment of the present disclosure, and FIG. 6 shows image data obtained by performing a scout scan on a lateral view of an object, according to an embodiment of the present disclosure.

As shown in FIGS. 5 and 6, image data for the shape of the object 30 includes at least one of image data for a top view of the object 30 and image data for a lateral view of the object 30.

In the CT apparatus 100 and the control method thereof according to the embodiments of the present disclosure, at least one of scout scan images of the top and lateral views of the object 30 may be acquired, and image data related to the shape of the object 30 may be acquired based on any one of the brightness and the intensity of image signals of the scout scan image.

That is, image data related to the shape of the object 30 can be acquired from scout scan images for the top and lateral views of the object 30, or image data related to the shape of the object 30 can be acquired from each scout scan image for the top or lateral view of the object 30.

Accordingly, as shown in FIG. 5, a scout scan can be performed on the top view of the object 30 to acquire a top view image R1 of a ROI of the object 30 requiring CT diagnosis, so that information about the width W of the object 30 can be acquired from the top view image R1. Also, a scout scan can be performed on the lateral view of the object 30 to acquire a lateral view image R2 of a ROI of the object 30 requiring CT diagnosis, so that information about the thickness T of the object 30 can be acquired from the lateral image R2.

In the CT apparatus 100 and the control method thereof according to the embodiments of the present disclosure, image data related to the shape of the object 30 acquired from a top view image and a lateral view image obtained by performing a scout scan on the object 30 can be compared to data about a top view image and a lateral view image among pre-stored data. This operation will be described in more detail with reference to the related drawings, later.

Figure 7:
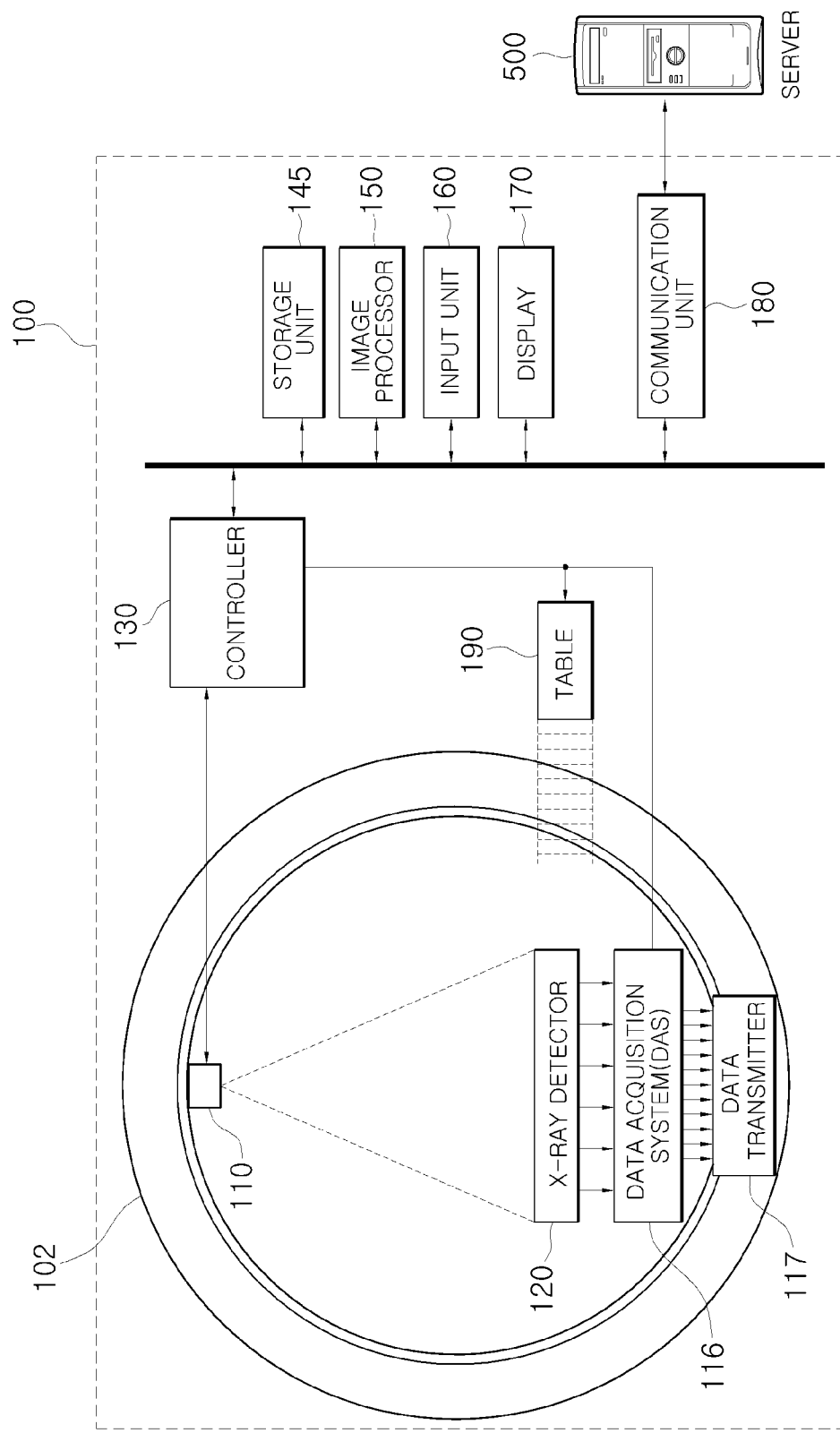
FIG. 7 illustrates a control block diagram showing control flow of a CT apparatus according to an embodiment of the present disclosure.

FIG. 7 is a control block diagram showing control flow of a CT apparatus according to an embodiment of the present disclosure.

As shown in FIG. 7, the CT apparatus 100 according to an embodiment of the present disclosure can include the gantry 102, the X-ray source 110, a Data Acquisition System (DAS) 116, a data transmitter 117, the X-ray detector 120, the controller 130, a storage unit 145, an image processor 150, an input unit 160, a display 170, and a communication unit 180.

As described above with reference to FIG. 1, the object 30 is placed on the table 190, and the table 190 can move in a predetermined direction (for example, at least one direction of up, down, left, and right directions), wherein the movement of the table 190 can be controlled by the controller 130.

Also, the gantry 102 can include a rotation frame (not shown), the X-ray source 110, the X-ray detector 120, the DAS 116, and the data transmitter 117. The gantry 102 can rotate at an angle of 180 degrees to 360 degrees around the bore 105 (see FIG. 1), and when the gantry 102 rotates, the X-ray source 110 and the X-ray detector 120 can also rotate accordingly.

The table 190 conveys the object 30 to be scanned to the inside of the bore 105. When a scout scan according to an embodiment of the present disclosure is performed, the table 190 can move in the D1 direction, and at this time, the gantry 102 can be fixed without rotating.

The X-ray source 110 generates X-rays, and irradiates the X-rays onto the object 30, and the X-ray detector 120 detects X-rays transmitted through the object 30.

The X-ray source 110 irradiates X-rays on the top and lateral views of the object 30 for a scout scan, as described above.

The X-ray detector 120 detects X-rays irradiated by the X-ray source 110 and then transmitted through the object 30. Also, the X-ray detector 120 converts the detected X-rays into electrical signals.

The X-ray detector 120 can be classified according to its material configuration, a method of converting detected X-rays into electrical signals, and a method of acquiring electrical signals.

First, the X-ray detector 120 can be classified into a mono type device or a hybrid type device according to its material configuration. If the X-ray detector 120 is a mono type device, a part of detecting X-rays and generating electrical signals, and a part of reading and processing the electrical signals can be semiconductors made of the same material, or may be manufactured by one process. If the X-ray detector 120 is a hybrid type device, a part of detecting X-rays and generating electrical signals, and a part of reading and processing the electrical signals may be made of different materials, or may be manufactured by different processes.

The X-ray detector 120 can use a direct conversion mode and an indirect conversion mode according to a method of converting X-rays into electrical signals. In the direct conversion mode, if X-rays are irradiated, electron-hole pairs can be temporarily generated in a light receiving device, electrons move to an anode, and holes move to a cathode by an electric field applied to both terminals of the light receiving device. The direct conversion mode is a method of converting the movement of the electrons and holes into electrical signals. In the indirect conversion mode, if X-rays irradiated from the X-ray source 70 react with a scintillator to emit photons having a wavelength of a visible light region, the light receiving device may detect the photons, and converts the photons into electrical signals.

Also, the X-ray detector 120 can use a Charge Integration Mode (CIM) of storing charges for a predetermined time period and then acquiring a signal from the stored charges, or a Photon Counting Mode (PCM) of counting the number of photons whenever a signal is generated by single X-ray photons, according to a method of acquiring electrical signals.

The DAS 116 can be connected to the X-ray detector 120, and electrical signals created by the X-ray detector 120 can be collected in the DAS 116 in a wired or wireless fashion. Also, the electrical signals created by the X-ray detector 120 can be provided to an analog-to-digital (A/D) converter (not shown) via an amplifier (not shown). A digital signal converted by the A/D converter can be provided to the image processor 150 through the data transmitter 120 in a wired or wireless fashion.

The controller 130 controls operations of the individual components included in the CT apparatus 100 according to an embodiment of the present disclosure. That is, the controller 130 can control operations of the X-ray source 110, the DAS 116, the data transmitter 117, and the table 190. Also, the controller 130 can control operations of the storage unit 145, the image processor 150, the input unit 160, the display 170, and the communication unit 180.

According to an embodiment of the CT apparatus 100, when a scout scan is performed on the object 30, the controller 130 can control the image processor 150 to acquire image data for the shape of the object 30, and compare the acquired image data to pre-stored image data to select at least one image data having greater similarity than predetermined similarity to the acquired image data from among the pre-stored image.

Also, the controller 130 can calculate a predicted dose of radiation required for scanning the object 30, that is, a dose of radiation to which the object 30 is expected to be actually exposed through a CT scan, based on a predetermined dose of radiation corresponding to the at least one image data selected by the image processor 150, and create a scanning protocol based on the calculated dose of radiation so that a CT scan can be performed on the object 30 according to the scanning protocol.

Furthermore, after the CT scan is performed on the object 30, the controller 130 can detect a dose of radiation to which the object 30 is actually exposed while the CT scan is performed, based on CT scan image data. The controller 130 can store the dose of radiation to which the object 30 is actually exposed, detected through the CT scan, in the storage unit 145, and update data stored in the storage unit 145 so as to use the data to predict a dose of radiation to which the object 30 is exposed, later. That is, the controller 130 can compare a dose of radiation to which the object 30 is expected to be exposed, calculated before a CT scan, to a dose of radiation to which the object 30 is actually exposed after the CT scan so as to calculate a difference, and then can correct the difference to reflect the corrected value when a CT scan is performed on the object 30 later.

The controller 130 can include a single general-purpose processor for performing all operations related to the functions of the CT apparatus 100, or can include a plurality of specialized processors, such as a communication processor for performing operations related to communications, a control processor for performing operations related to control functions, etc.

The storage unit 145 stores various kinds of data related to operations of the CT apparatus 100. That is, the storage unit 145 can store image data for the shape of the object 30, related to a CT scan. The stored image data for the shape of the object 30 can be image data for the shape of a patient who is a target to be CT-scanned, or image data for the shape of another object which is not a target to be scanned. Also, the stored image data for the shape of the object 30 can be image data for the shape of a phantom.

That is, the image data stored in the storage unit 145 may be a plurality of data about at least one object 30. Also, the stored image data can be provided to the image processor 150, and compared to image data for the shape of the object 30, acquired through a scout scan performed on the object 30 by the CT apparatus 100.

The image data stored in the storage unit 145 can be image data for the top view of the object 30 and image data for the lateral view of the object 30. Also, the image data may be one of projection profile data of the object 30, bone structure image data of the object 30, and contour image data of the object 30, which will be described later. That is, the image data may be one of projection profile data, bone structure image data, and contour image data for each of the top and lateral views of the object 30.

In the storage unit 145, a dose of radiation can be stored to correspond to each image data for the shape of at least one object. That is, when a CT scan is performed on an object 30 having a shape corresponding to stored image data, a predicted value for a dose of radiation to which the object 30 is actually exposed upon the CT scan may be stored in the storage unit 145. The dose of radiation may correspond to a dose of radiation enabling a CT scan to be performed on the corresponding object 30 with a low dose as possible, while optimizing the quality of an image to be acquired through the CT scan of the object 30. The dose of radiation stored in the storage unit 145 may be data about a dose of radiation to be used to perform a CT scan on the object 30, calculated in consideration of the influence of scattered radiation, as described above.

Also, the storage unit 145 can store a reference value of similarity to be used to determine a degree of similarity when image data for the shape of the object 30 to be CT-scanned is compared to pre-stored image data. Furthermore, data determined to be similar to the image data for the shape of the object 30 to be CT-scanned, among the pre-stored image data, may also be stored in the storage unit 145.

After a CT scan is performed on the object 30, additional image data for the shape of the object 30 can be acquired, and in this case, the additional image data may also be stored in the storage unit 145. Also, the controller 130 can detect a dose of radiation included in the CT-scanned object 30 based on the additional image data, and store the detected dose of radiation of the object 30 in the storage unit 145.

In addition, various kinds of data acquired through a scout scan performed on the object 30, and various kinds of data acquired through a CT scan performed on the object 30 can be stored in the storage unit 145. Also, according to an embodiment of the present disclosure, data can be stored in real time in the storage unit 145 according to the performance results of a scout scan or a CT scan. The stored data can be updated in real time so as to be used to improve the accuracy of a predicted dose of radiation for the object 30. That is, the storage unit 145 can store a difference obtained by comparing a dose of radiation to which the object 30 is expected to be exposed, calculated before a CT scan, to a dose of radiation to which the object 30 is actually exposed after the CT scan.

The storage unit 145 can include at least one type of storage medium among a flash memory type, a hard disk type, a multimedia card micro type, card type memory (for example, a Secure Digital (SD) card or an eXtreme Digital (XD) card), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disk, and an optical disk.

The image processor 150 can receive data (for example, raw data not processed) acquired from the DAS 116 through the data transmitter 117, and perform pre-processing on the data.

The pre-processing can include, for example, a process for correcting sensitivity unevenness between channels, and a process for correcting a sharp reduction in signal intensity or signal loss due to an X-ray absorber such as metal, etc. Output data of the image processor 150 may be referred to as raw data or projection data. The projection data can be stored in the storage unit 145, together with scanning conditions (for example, a tube voltage, a scanning angle, etc.) applied when the projection data is acquired.

Also, the image processor 150 can reconstruct a section image for the object 30 using a set of the acquired projection data. The section image can be a 3D image. In other words, the image processor 150 can create a 3D image for the object 30 using a cone beam reconstruction method, etc., based on a set of the acquired projection data. Image data created by the image processor 150 can be transferred to the display 170, and the display 170 may display the section image of the object.

According to an embodiment of the present disclosure, the image processor 150 acquires image data for the shape of the object 30 based on a scout scan image acquired by the scanner including the X-ray source 110 and the X-ray detector 120, and compares the image data to image data stored in advance in the storage unit 145. The image processor 150 can select at least one image data having greater similarity than predetermined similarity to the acquired image data from among the pre-stored image data, according to the result of the comparison.

The image data for the shape of the object 30, acquired by the image processor 150 can include image data for the top and lateral views of the object 30, and can include at least one of projection profile data, bone structure image data, and contour image data for each of the top and lateral views of the object 30, as described above.

The image processor 150 can acquire projection profile data of the object 30, based on any one of the brightness and the intensity of image signals of a scout scan image acquired by performing a scout scan on the object 30. Also, the image processor 150 can create at least one of bone structure image data and contour image data of the object 30 by performing image processing on the projection profile data of the object 30.

The image processor 150 can compare the image data acquired by the above-described method to pre-stored image data. That is, the image processor 150 can compare the acquired projection profile data to pre-stored projection profile data, the acquired bone structure image data to pre-stored bone structure image data, and the acquired contour image data to pre-stored contour image data.

Also, when a CT scan is performed on the object 30, the image processor 150 can acquire image data of the CT-scanned object 30 according to the result of the CT scan.

The input unit 160 can receive control commands for overall operations of the CT apparatus 100, including a command for moving the table 190 on which the object 30 is placed, a command for selecting a X-ray scan mode, a command for selecting X-ray scanning conditions, a command for displaying a scanned image, etc. For example, the X-ray scanning conditions can include a plurality of tube voltages, an energy value of a plurality of X-rays, a scanning protocol, an image reconstruction method, a Field Of View (FOV) area, an image post-processing parameter, etc. Also, the image processing conditions can include resolution of images, an attenuation coefficient for images, a combination ratio of images, etc.

The input unit 160 can include a device for receiving predetermined inputs from the outside. For example, the input unit 160 can include a microphone, a keyboard, a mouse, a joystick, a touch pad, a touch pen, a voice recognition device, a gesture recognition device, etc. The configuration of the input unit 160 has been described above with reference to FIG. 1, and accordingly, further descriptions thereof will be omitted.

The display 170 can display a screen for supporting the user to input control commands, a screen showing a controlled status of the CT apparatus 100, or images created by the image processor 150. The configuration of the display 170 has been described above with reference to FIG. 1, and accordingly, further descriptions thereof will be omitted.

The communication unit 180 can communicate with an external device or external medical equipment through a server 500, etc. That is, the communication unit 180 can be connected to a network in a wired or wireless fashion to communicate with the external server 500, medical equipment, or a mobile terminal. Also, the communication unit 180 can transmit/receive data to/from a hospital server or another medical equipment in a hospital, connected through the Picture Achieving and Communication System (PACS).

The communication unit 180 can perform data communications with a mobile terminal, etc. according to the Digital Imaging and Communications in Medicine (DI-COM) standard. The communication unit 180 can transmit and receive data related to X-ray scanning and diagnosis of the object 30 through the network. Also, the communication unit 180 can transmit information about whether the CT apparatus 100 operates properly or wrongly and information about the current quality-managed state of the CT apparatus 100 to a system manager or a service manager through the network, and receive feedbacks from the system manager or the service manager through the network.

Also, the communication unit 180 can transmit various kinds of data related to operations of the CT apparatus 100, which can be stored in the storage unit 145, to the external server 500, and various kinds of data according to an embodiment of the present disclosure can be stored in an external device or the external server 500. The external server 500 can store data related to a predicted dose of radiation to which the object 30 is exposed, and the data can be updated in real time and provided to the controller 130 through the communication unit 180.

Figure 8A:
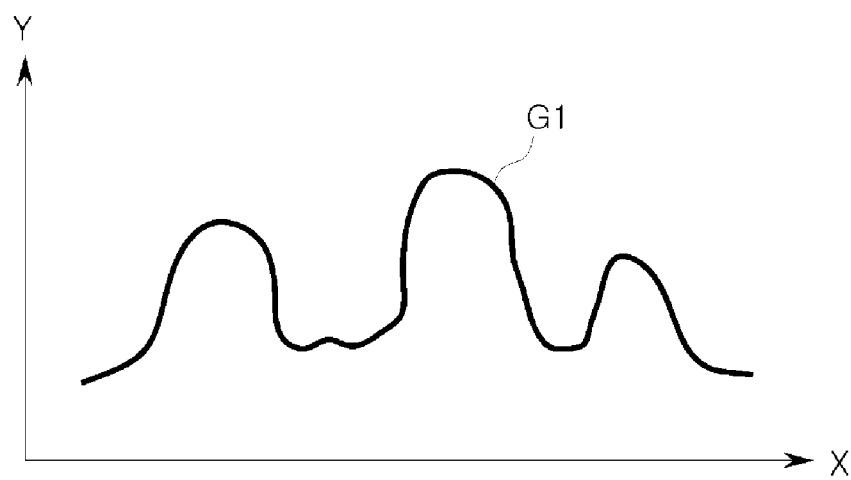
FIG. 8A illustrates image data for a projection profile of a top view of an object, acquired according to an embodiment of the present disclosure.
Figure 8A:
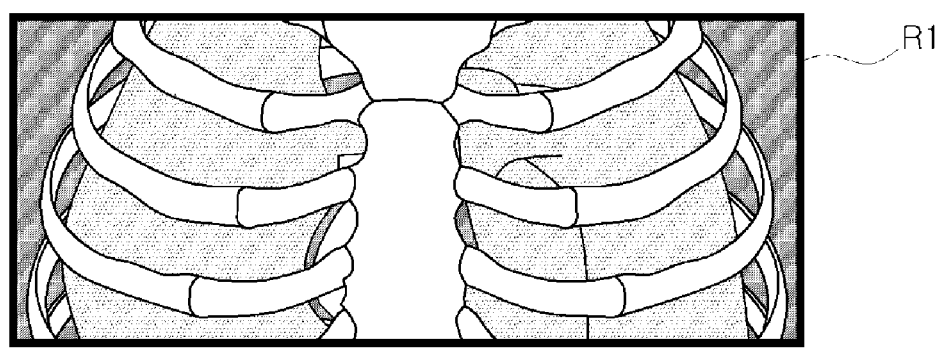
Figure 8B:
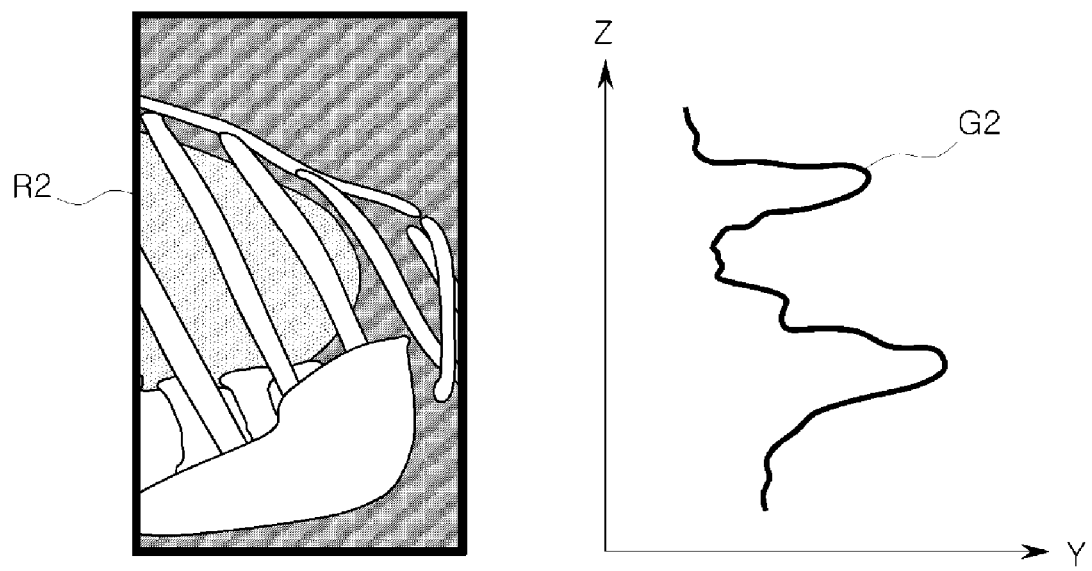
FIG. 8B illustrates image data for a projection profile of a lateral view of an object, acquired according to an embodiment of the present disclosure.

FIG. 8A shows image data for a projection profile of a top view of an object, acquired according to an embodiment of the present disclosure, and FIG. 8B shows image data for a projection profile of a lateral view of an object, acquired according to an embodiment of the present disclosure.

As described above with reference to FIG. 7, if a scout scan is performed on the object 30, the image processor 150 can acquire image data for the shape of the object 30. That is, if a scout scan is performed on a top view of the object 30, the image processor 150 can acquire image data for a projection profile of a target region R1 of the top view image shown in FIG. 5.

The projection profile for the top view of the object 30, acquired by the image processor 150 can be represented in the form of a graph G1 shown in FIG. 8A. FIG. 8A shows an example in which the object 30 is a human's chest. Referring to FIG. 8A, an image for the top view of the object 30, acquired by the image processor 150 may be displayed as an image R1 including bones and organs. Since degrees of transmission, reflection, and absorption of a low dose of X-rays irradiated for a scout scan depend on the kinds of materials (for example, bones, organs, etc.) constituting the object 30, the brightness and the intensity of image signals of the image data of the object 30 may be also different according to the kinds of materials (for example, bones, organs, etc.) constituting the object 30.

The projection profile data of the object 30 can be displayed in the form of a graph G1 according to the intensities of image pixels based on the brightness and image signals of the image data. The projection profile data displayed in the form of the graph G1 can be based on the brightness of the top view image data of the object 30, based on the intensities of the image signals, or based on both the brightness of the top view image data of the object 30 and the intensities of the image signals.

Also, the graph form of the projection profile data such as the graph G1 shown in FIG. 8A is only exemplary, and the projection profile data can be displayed in various forms according to factors deciding the projection profile data.

Accordingly, the image processor 150 can perform a scout scan on the top view of the object 30 to acquire image data such as R1, and analyze the acquired image data to acquire projection profile data such as G1.

Referring to FIG. 8B, if a scout scan is performed on a lateral view of the object 30, the image processor 150 can acquire image data for a projection profile of a target region R2 of the lateral view image shown in FIG. 6.

The projection profile for the lateral view of the object 30, acquired by the image processor 150 can be represented in the form of a graph G2. As described above with reference to FIG. 8A, projection profile data for the lateral view of the object 30 can be displayed in the form of the graph G2 according to the intensities of image pixels based on the brightness and image signals of the image data. The projection profile data displayed in the form of the graph G2 can be based on the brightness of the lateral view image data of the object 30, based on the intensities of the image signals, or based on both the brightness of the lateral view image data of the object 30 and the intensities of the image signals.

Also, the projection profile data for the lateral view of the object 30 can be displayed in any other various forms, instead of a graph form such as G2.

Accordingly, the image processor 150 can perform a scout scan on the lateral view of the object 30 to acquire image data such as R2, and analyze the acquired image data to acquire projection profile data such as G2.

The image data for the projection profiles of the top and lateral views of the object 30 shown in FIGS. 8A and 8B can be stored in the storage unit 145, and used to be compared to pre-stored image data corresponding to the projection profiles.

Figure 9A:
FIG. 9A illustrates image data for a bone structure of a top view of an object, acquired according to an embodiment of the present disclosure.
Figure 9B:
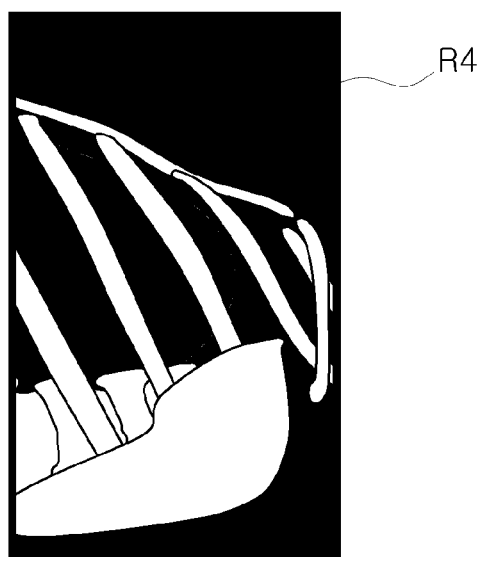
FIG. 9B illustrates image data for a bone structure of a lateral view of an object, acquired according to an embodiment of the present disclosure.

FIG. 9A shows image data for a bone structure of a top view of an object, acquired according to an embodiment of the present disclosure, and FIG. 9B shows image data for a bone structure of a lateral view of an object, acquired according to an embodiment of the present disclosure.

The image processor 150 can perform image processing on the projection profile data for the top view of the object 30, as shown in FIG. 8A, to acquire image data for a bone structure of the object 30, as shown in FIG. 9A.

That is, in FIG. 8A, an image for the top view of the object 30, acquired by the image processor 150 can be displayed as an image (that is, the image R1) including all of bones and organs, however, in FIG. 9A, only the bones except for the organs may be extracted from the image R1 and displayed. That is, since the brightness, the intensity of image signals, etc. of image data for bones constituting the object 30 are different from those for organs constituting the object 30, the image processor 150 can perform image processing for extracting image data for only bones.

The image processor 150 can extract image data for only bones to create image data (that is, R3) for the bone structure of the top view of the object 30, and the created image data may be stored in the storage unit 145.

Since anatomical features such as the positions, thicknesses, etc. of the bones constituting the object 30 depend on the kind of the object 30, the image data for the bone structure as shown in FIG. 9A can be compared to image data for the bone structures of other objects stored in advance in the storage unit 145, based on such anatomical features.

Also, the image processor 150 can perform image processing on the projection profile data for the lateral view of the object 30, as shown in FIG. 8B, to acquire image data for a bone structure of the object 30, as shown in FIG. 9B.

That is, the image processor 150 can extract image data for only bones to create image data (that is, R4) for the bone structure of the lateral view of the object 30, and the created image data may be stored in the storage unit 145.

Figure 10A:
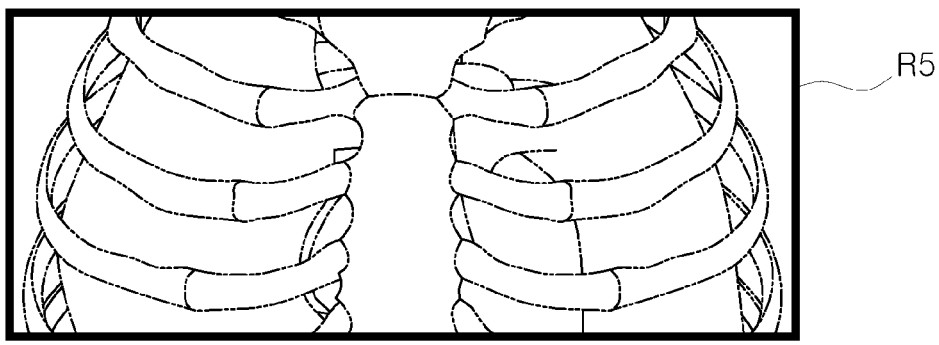
FIG. 10A illustrates contour image data for a top view of an object, acquired according to an embodiment of the present disclosure.
Figure 10B:
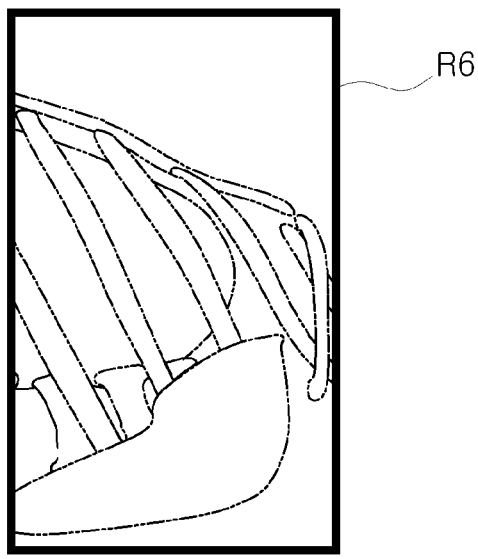
FIG. 10B illustrates contour image data for a lateral view of an object, acquired according to an embodiment of the present disclosure.

FIG. 10A shows contour image data for a top view of an object, acquired according to an embodiment of the present disclosure, and FIG. 10B shows contour image data for a lateral view of an object, acquired according to an embodiment of the present disclosure.

The image processor 150 can perform image processing on the projection profile data for the top view of the object 30, as shown in FIG. 8A, to acquire contour image data R5 for the top view of the object 30, as shown in FIG. 10A.

The contour image data can correspond to data resulting from extracting information about the outlines of bones or organs from image data obtained by scanning the object 30. That is, by extracting the outlines of the bones of the object 30 and the outlines of the organs of the object 30 to image the outlines of the bones and the outlines of the organs, it is possible to determine similarity to other data based on the positions of anatomical factors constituting the object 30.

Accordingly, the image processor 150 can perform image processing for extracting the outlines of bones or organs included in the object 30, based on image data obtained by performing a scout scan on the top view of the object 30, to reconstruct the image data as image data representing the outlines of the object 30. The image data R5 for the top view contour of the object 30, acquired by the image processor 150 can be stored in the storage unit 145.

Since anatomical features such as the positions, sizes, etc. of bones or organs constituting the object 30 depend on the kind of the object 30, the image data representing the contour of the object 30, as shown in FIG. 10A, may be compared to image data about the contours of other objects stored in advance in the storage unit 145 based on such anatomical features.

Also, the image processor 150 can perform image processing on the projection profile data for the lateral view of the object 30, as shown in FIG. 8B, to acquire contour image data R6 for the lateral view of the object 30, as shown in FIG. 10B.

That is, the image processor 150 can perform image processing for extracting the outlines of bones or organs shown when the lateral view of the object 30 is scanned, based on image data obtained by performing a scout scan on the lateral view of the object 30, to reconstruct the image data as image data representing the contour of the object 30. The image data R6 for the lateral contour of the object 30, acquired by the image processor 150 may be stored in the storage unit 145.

Since anatomical features such as the positions, sizes, etc. of bones or organs constituting the lateral view of the object 30 are different from those of bones or organs constituting the lateral view of another object, the image data representing the lateral view contour of the object 30 may be compared to image data about the contours of other objects stored in advance in the storage unit 145, based on such anatomical features.

Figure 11A:
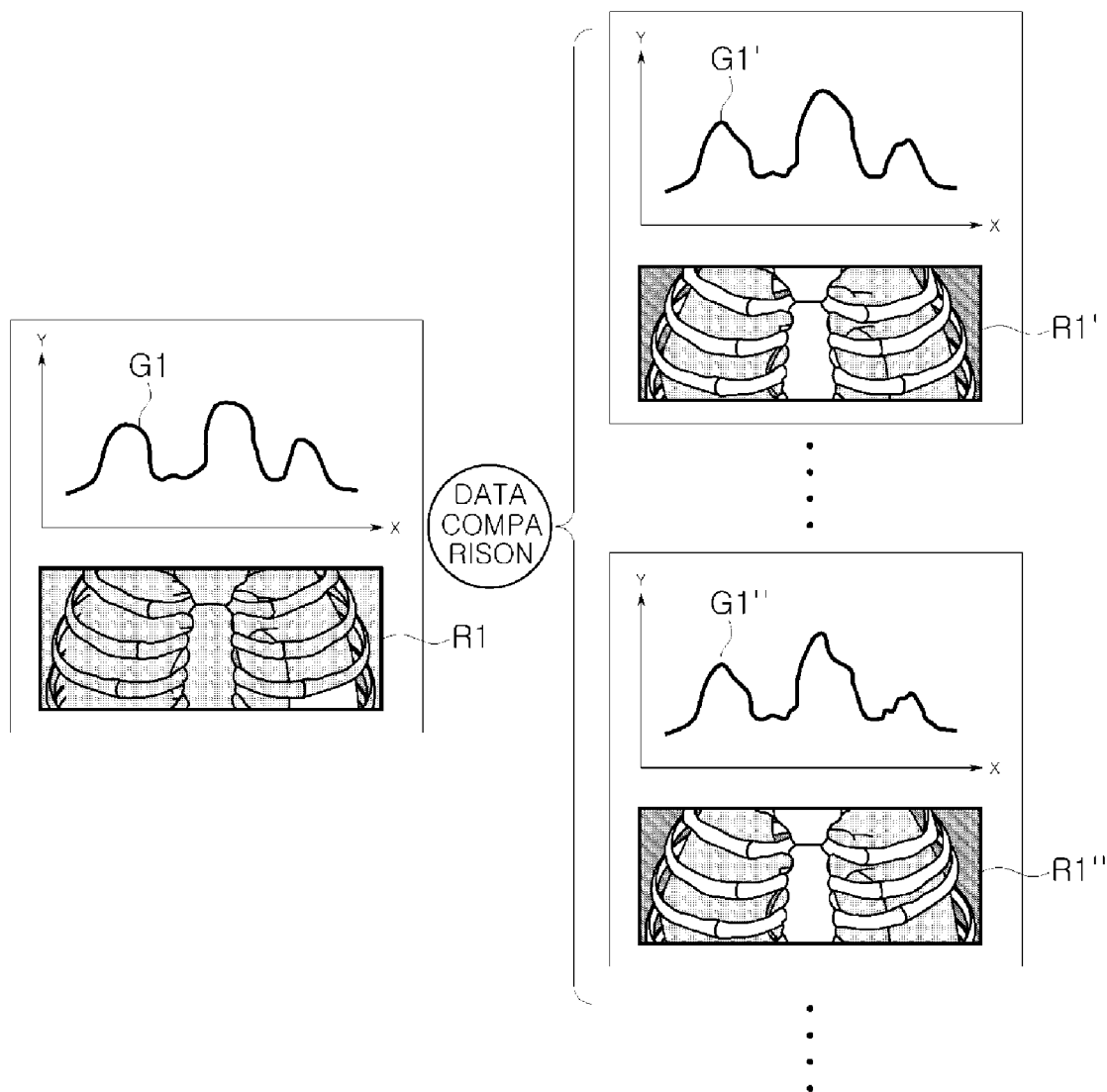
FIG. 11A illustrates a conceptual view for describing operation in which an image processor compares image data for a projection profile of a top view of an object, acquired according to an embodiment of the present disclosure, to pre-stored image data.
Figure 11B:
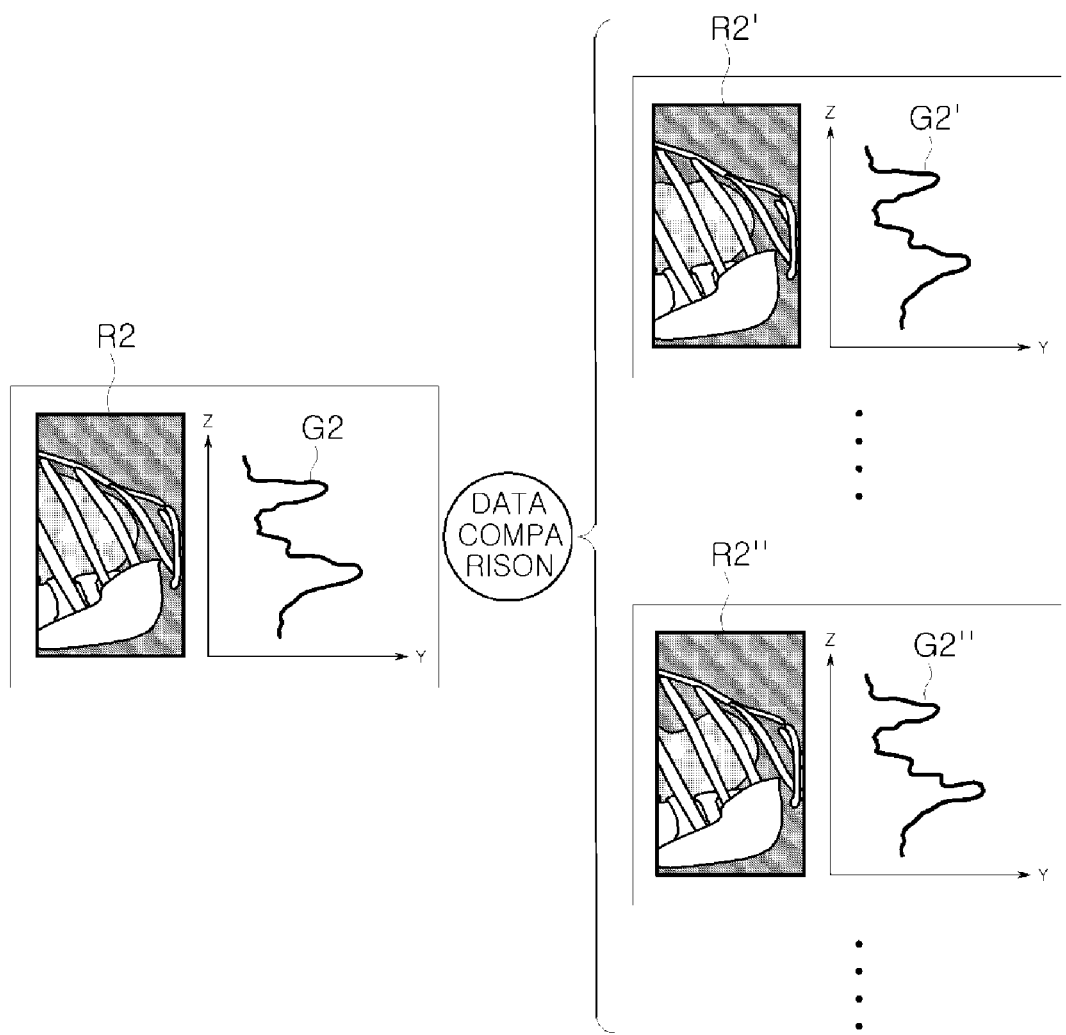
FIG. 11B illustrates a conceptual view for describing operation in which an image processor compares image data for a projection profile of a lateral view of an object, acquired according to an embodiment of the present disclosure, to pre-stored image data.

FIG. 11A is a conceptual view for describing operation in which an image processor compares image data for a projection profile of a top view of an object, acquired according to an embodiment of the present disclosure, to pre-stored image data, and FIG. 11B is a conceptual view for describing operation in which an image processor compares image data for a projection profile of a lateral view of an object, acquired according to an embodiment of the present disclosure, to pre-stored image data.

If a scout scan is performed on a top view of the object 30, the image processor 150 may acquire projection profile data G1 for the target region R1 of the top view of the object 30, as described above with reference to FIG. 8A.

The image processor 150 can compare the acquired projection profile data G1 to a plurality of projection profile data stored in advance in the storage unit 145.

Since degrees of transmission, reflection, and absorption of a low dose of X-rays irradiated for a scout scan depend on bones, organs, etc. constituting the object 30, the brightness and the intensity of image signals of the image data of the object 30 may be different according to the bones, organs, etc. constituting the object 30. Accordingly, projection profile data of the object 30 can be displayed in the form of a graph G1.

The storage unit 145 can store scout scan image data for a plurality of different objects or phantoms, and can also store a plurality of projection profile data based on the scot scan image data.

In order to acquire information about another object having a similar shape to the scout-scanned object 30, the image processor 150 can compare projection profile data R1 obtained by performing a scout scan on the object 30 to stored projection profile data of a plurality of other objects. If the image processor 150 determines that the projection profile data R1 of the object 30 is similar to the projection profile data of another object, the image processor 150 can determine that the shape of the object 30 is similar to that of the other object.

Referring to FIG. 11A, the image processor 150 can decide projection profile data G1' and G1" among the plurality of projection profile data stored in the storage unit 145, as data similar to projection profile data of the object 30 acquired through the scout scan.

That is, the storage unit 145 can store a reference value of predetermined similarity for determining similarity of image data. The image processor 150 can select at least one projection profile data having greater similarity than the predetermined similarity from among the plurality of pre-stored projection profile data.

As shown in FIG. 11A, the projection profile data G1 for the top view of the object 30, acquired through a scout scan can correspond to the top view image data R1, and the projection profile data G1' and G1" having greater similarity than the predetermined similarity may correspond to top view image data R1' and R1". The image data R1, R1', and R1" may have small differences as shown in FIG. 11A.

Accordingly, the shape of the scout-scanned object 30 can be most similar to those of objects corresponding to the top view image data R1' and R1" selected based on the similarity of the projection profile data for the top view.

Referring to FIG. 11B, if a scout scan is performed on the lateral view of the object 30, the image processor 150 can acquire projection profile data G2 for the target region R2 of the lateral view image of the object 30, as described above with reference to FIG. 8B.

The image processor 150 can compare the projection profile data G2 acquired for the lateral view image to a plurality of projection profile data stored in advance in the storage unit 145. That is, in order to acquire information about another object having a similar shape to the object 30 whose lateral view is scout-scanned, the image processor 150 can compare the projection profile data R2 acquired through the scout scan performed on the lateral view of the object 30, to projection profile data for the lateral views of a plurality of other objects. If the image processor 150 determines that the projection profile data R2 is similar to projection profile data for a lateral view of another object, the image processor 150 can determine that the lateral view of the object 30 is similar to that of the other object.

Referring to FIG. 11B, the image processor 150 can decide projection profile data having the similar shape to G2' and G2" among the plurality of projection profile data stored in the storage unit 145, as data similar to projection profile data G2 for the lateral view of the object 30 obtained through a scout scan.

The projection profile data G2 for the lateral view of the object 30, acquired through the scout scan may correspond to lateral view image data R2, and projection profile data G2' and G2" having greater similarity than predetermined similarity to the projection profile data G2 may correspond to lateral view image data R2' and R2".

Accordingly, the shape of the scout-scanned object 30 can be most similar to those of objects corresponding to the lateral view image data R2' and R2" selected based on similarity to the projection profile data G2 for the lateral view.

Figure 12A:
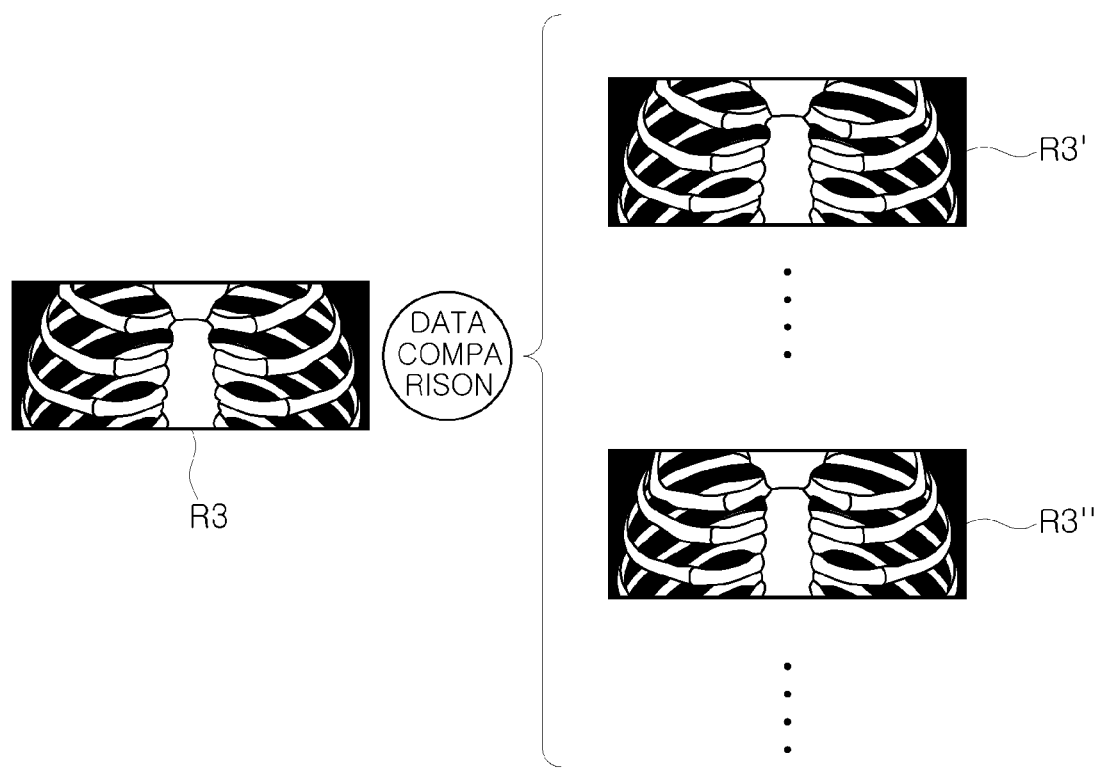
FIG. 12A illustrates a conceptual view for describing operation in which an image processor compares image data for a bone structure of a top view of an object, acquired according to an embodiment of the present disclosure, to pre-stored image data.
Figure 12B:
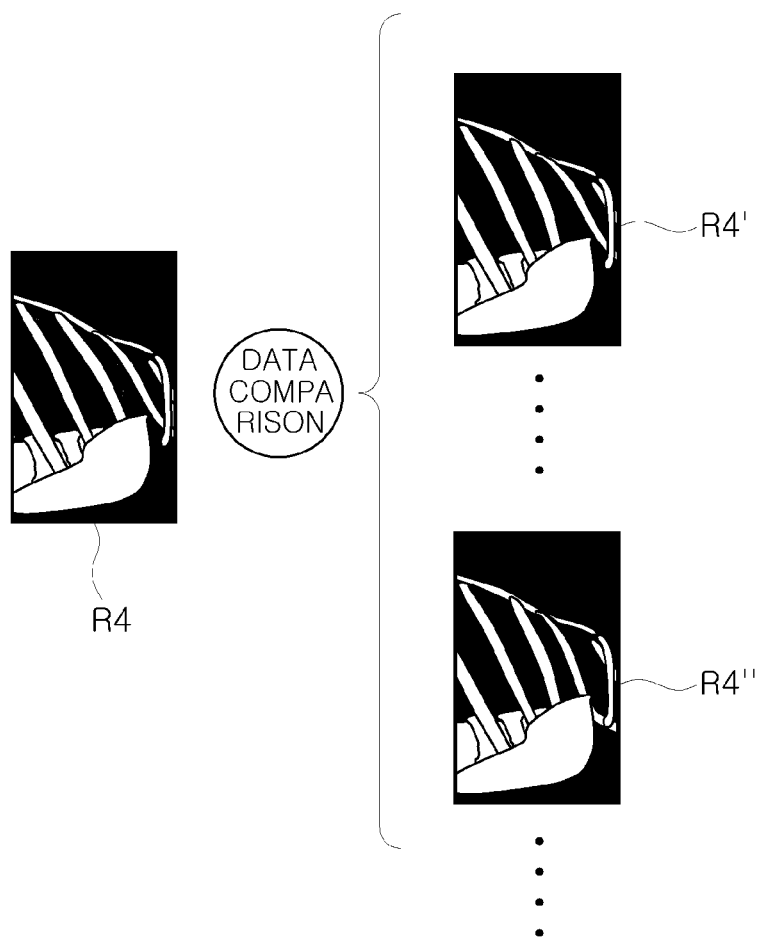
FIG. 12B illustrates a conceptual view for describing operation in which an image processor compares image data for a bone structure of a lateral view of an object, acquired according to an embodiment of the present disclosure, to pre-stored image data.

FIG. 12A is a conceptual view for describing operation in which an image processor compares image data for a bone structure of a top view of an object, acquired according to an embodiment of the present disclosure, to pre-stored image data, and FIG. 12B is a conceptual view for describing operation in which an image processor compares image data for a bone structure of a lateral view of an object, acquired according to an embodiment of the present disclosure, to pre-stored image data.

If a scout scan is performed on a top view of the object 30, the image processor 150 can acquire image data R3 for a bone structure of a top view image of the object 30, as described above with reference to FIG. 9A.

Then, the image processor 150 can compare the acquired image data R3 for the bone structure to a plurality of bone structure image data stored in advance in the storage unit 145.

That is, since the brightness, the intensity of image signals, etc. of image data for bones constituting the object 30 are different from those for organs constituting the object 30, the image processor 150 can perform image processing for extracting image data for bones, as described above, to create image data (for example, R3) for a bone structure of the top view of the object 30.

The storage unit 145 can store scout scan image data for a plurality of different objects or phantoms, and also can store a plurality of bone structure image data based on the scout scan image data.

In order to acquire information about another object having a similar shape to the scout-scanned object 30, the image processor 150 can compare the bone structure image data R3 acquired by performing a scout scan on the object 30 to pre-stored bone structure image data of a plurality of other objects. That is, if the bone structure image data R3 is similar to the bone structure image data of another object, the image processor 150 can determine that the bone structure of the scout-scanned object 30 is similar to the bone structure of the other object.

Referring to FIG. 12A, the image processor 150 can decide bone structure image data R3' and R3" among a plurality of bone structure image data stored in the storage unit 145, as data similar to the bone structure image data R3 of the object 30 obtained through the scout scan.

That is, the image processor 150 can select at least one bone structure image data having greater similarity than predetermined similarity to the bone structure image data R3 of the object 30, from among a plurality of bone structure image data stored in the storage unit 145.

Referring to FIG. 12A, the bone structure image data R3 for the top view of the object 30, acquired through the scout scan can be most similar to the bone structure image data R3' and R3" stored in the storage unit 145 and having greater similarity than the predetermined similarity to the bone structure image data R3 of the object 30, although the bone structure image data R3 has small differences from the bone structure image data R3' and R3".

Accordingly, the shape of the scout-scanned object 30 can be most similar to those of objects corresponding to the bone structure image data R3' and R3" selected based on similarity to the bone structure image data R3 for the top view.

If a scout scan is performed on the lateral view of the object 30, the image processor 150 may acquire bone structure image data R4 for a lateral view image of the object 30, as described above with reference to FIG. 9B.

The image processor 150 can compare the acquired bone structure image data R4 to a plurality of bone structure image data stored in advance in the storage unit 145. That is, in order to acquire information about another object having the similar shape to the lateral view of the scout-scanned object 30, the image processor 150 can compare the bone structure image data R4 acquired by performing a scout scan on the object 30 to pre-stored bone structure image data of a plurality of other objects.

Referring to FIG. 12B, the image processor 150 can decide bone structure image data R4' and R4" for the lateral view among the plurality of bone structure image data stored in the storage unit 145, as data similar to the bone structure image data R4 of the object 30 acquired through the scout scan for the lateral view.

That is, the image processor 150 can select at least one bone structure image data having greater similarity than predetermined similarity to the bone structure image data R4 of the object 30, from among a plurality of bone structure image data for the lateral view of the object 30, stored in the storage unit 145.

Referring to FIG. 12B, the bone structure image data R4 for the lateral view of the object 30 acquired through the scout scan can be most similar to the bone structure image data R4' and R4" stored in the storage unit 145 and having greater similarity than the predetermined similarity to the bone structure image data R4 of the object 30, although the bone structure image data R4 has small differences from the bone structure image data R4' and R4".

Accordingly, the shape of the scout-scanned object 30 may be most similar to those of objects corresponding to the bone structure image data R4' and R4" selected based on similarity to the bone structure image data R4 for the lateral view.

Figure 13A:
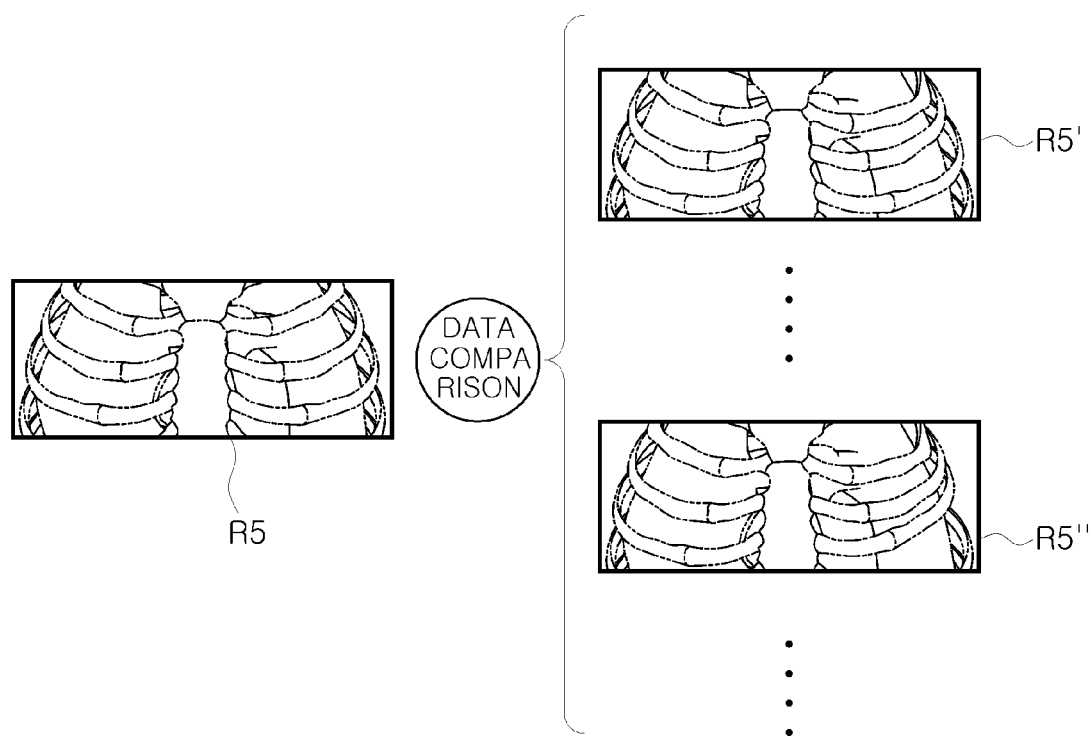
FIG. 13A illustrates a conceptual view for describing operation in which an image processor compares contour image data for a top view of an object, acquired according to an embodiment of the present disclosure, to pre-stored data.
Figure 13B:
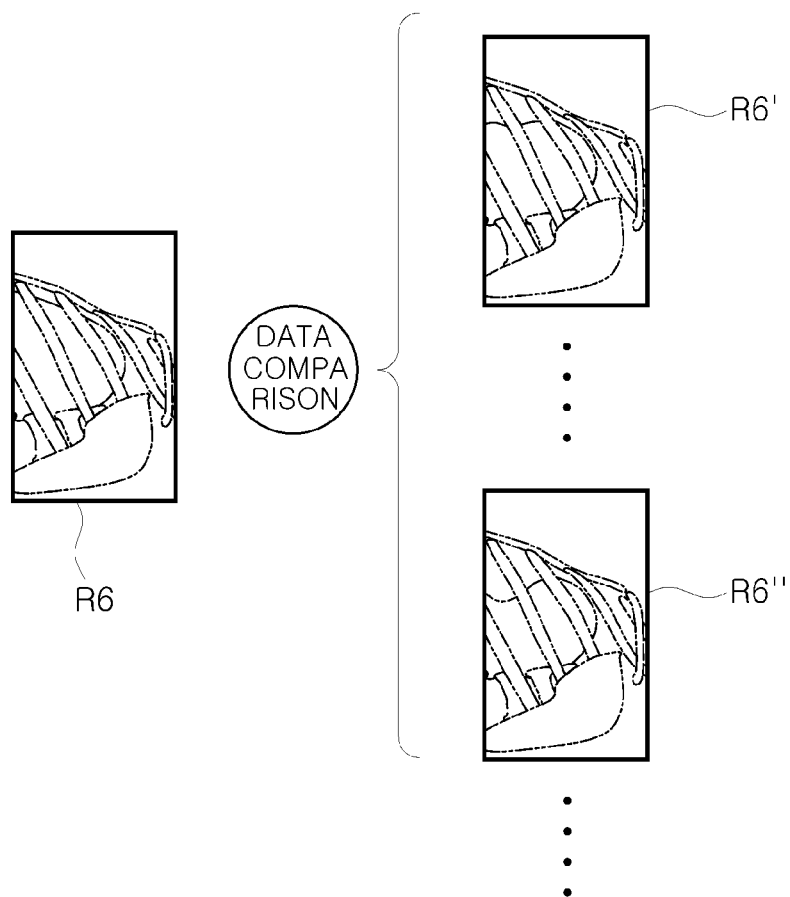
FIG. 13B illustrates a conceptual view for describing operation in which an image processor compares contour image data for a lateral view of an object, acquired according to an embodiment of the present disclosure, to pre-stored data.

FIG. 13A is a conceptual view for describing operation in which an image processor compares contour image data for a top view of an object, acquired according to an embodiment of the present disclosure, to pre-stored data, and FIG. 13B is a conceptual view for describing operation in which an image processor compares contour image data for a lateral view of an object, acquired according to an embodiment of the present disclosure, to pre-stored data.

If a scout scan is performed on a top view of the object 30, the image processor 150 can perform image processing on projection profile data for the top view of the object 30 to acquire contour image data R5 for the top view, as described above with reference to FIG. 10A.

The image processor 150 can compare the acquired contour image data R5 to a plurality of contour image data stored in advance in the storage unit 145.

As described above, the image processor 150 can perform image processing for extracting the outlines of the bones and organs of the object 30 to image the results of the extraction, thereby creating contour image data R5 for the top view of the object 30.

The storage unit 145 can store scout scan image data for a plurality of different objects or phantoms, and can also store a plurality of projection profile data based on the scot scan image data.

In order to acquire information about another object having a similar shape to the scout-scanned object 30, the image processor 150 can compare the contour image data R5 obtained by performing a scout scan on the object 30 to pre-stored contour image data of a plurality of other objects. If the image processor 150 determines that the contour image data R5 of the object 30 is similar to the contour image data of another object, the image processor 150 can determine that the contours of the bones and organs of the object 30 are similar to those of the other object.

Referring to FIG. 13A, the image processor 150 can decide contour image data R5' and R5" among a plurality of contour image data stored in the storage unit 145, as data similar to the contour image data R5 of the object 30 acquired through the scout scan.

That is, the image processor 150 can select at least one contour image data having greater similarity than predetermined similarity to the contour image data R5 of the object 30, from among a plurality of contour image data stored in the storage unit 145.

As shown in FIG. 13A, the contour image data R5 for the top view of the object 30, acquired through the scout scan may be most similar to the contour image data R5' and R5" stored in the storage unit 145 and having greater similarity than the predetermined similarity to the contour image data R5 of the object 30, although the contour image data R5 has small differences from the contour image data R5' and R5".

Accordingly, the shape of the scout-scanned object 30 can be most similar to those of objects corresponding to the contour image data R5' and R5" selected based on similarity to the projection profile data R5 for the top view of the object 30.

if a scout scan is performed on a lateral view of the object 30, the image processor 150 can perform image processing on projection profile data for the lateral view of the object 30 to acquire contour image data R6 for the lateral view of the object 30, as described above with reference to FIG. 10B.

The image processor 150 can compare the acquired contour image data R6 to a plurality of contour image data stored in advance in the storage unit 145. That is, in order to acquire information about another object having the similar shape to the lateral view of the scout-scanned object 30, the image processor 150 can compare the contour image data R6 acquired by performing the scout scan on the object 30, to pre-stored contour image data of a plurality of other objects.

Referring to FIG. 13B, the image processor 150 can decide contour image data R6' and R6" for the lateral view, among the plurality of contour image data stored in the storage unit 145, as data similar to the contour image data R6 of the object 30 acquired through the scout scan for the lateral view.

That is, the image processor 150 can select at least one contour image data having greater similarity than the pre-determined similarity to the contour image data R6 of the object 30, from among the plurality of contour image data for the lateral view of the object 30, stored in the storage unit 145.

Referring to FIG. 13B, the contour image data R6 for the lateral view of the object 30, acquired through the scout scan can be most similar in the contours of bones and organs to the contour image data R6' and R6" stored in the storage unit 145 and having greater similarity than predetermined similarity to the contour image data R6 of the object 30, although the contour image data R6 has small differences from the contour image data R6' and R6".

Figure 14:
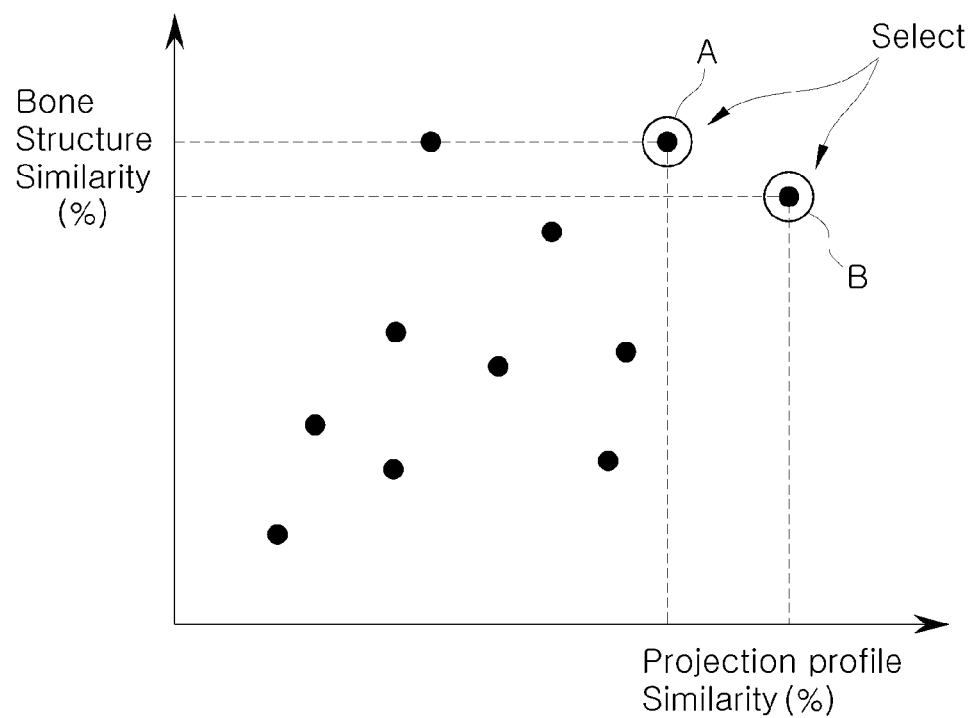
FIGS. 14, 15, and 16 illustrate conceptual views for describing operation of comparing image data for the shape of an object, acquired through a scout scan according to an embodiment of the present disclosure, to pre-stored image data to select at least one image data having greater similarity than predetermined similarity.
Figure 15:
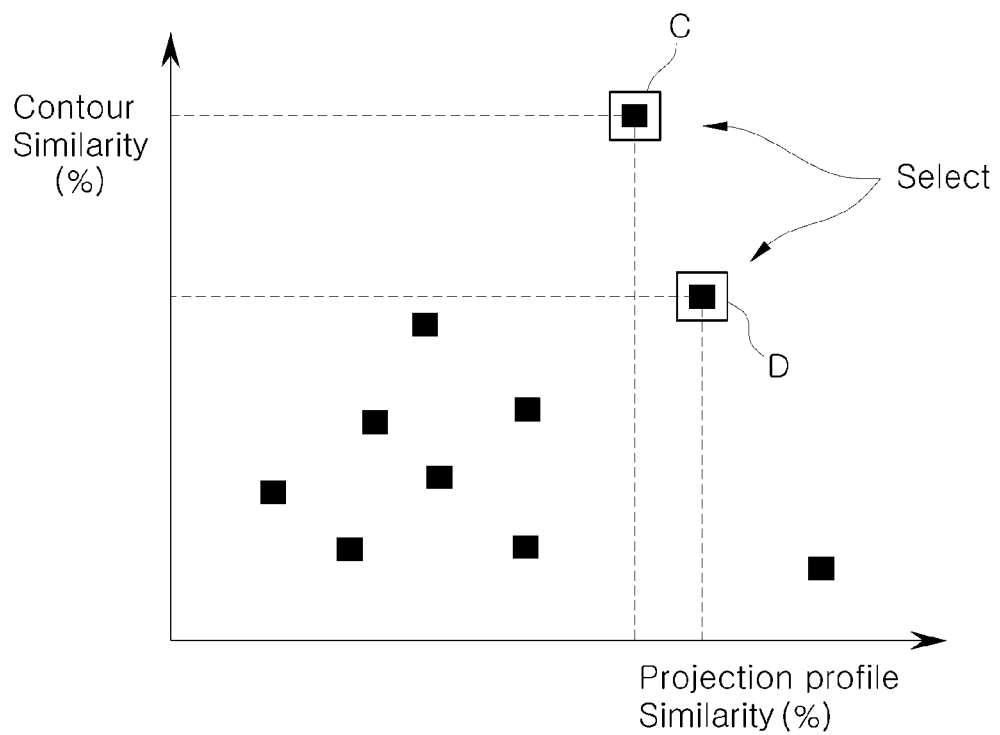
Figure 16:
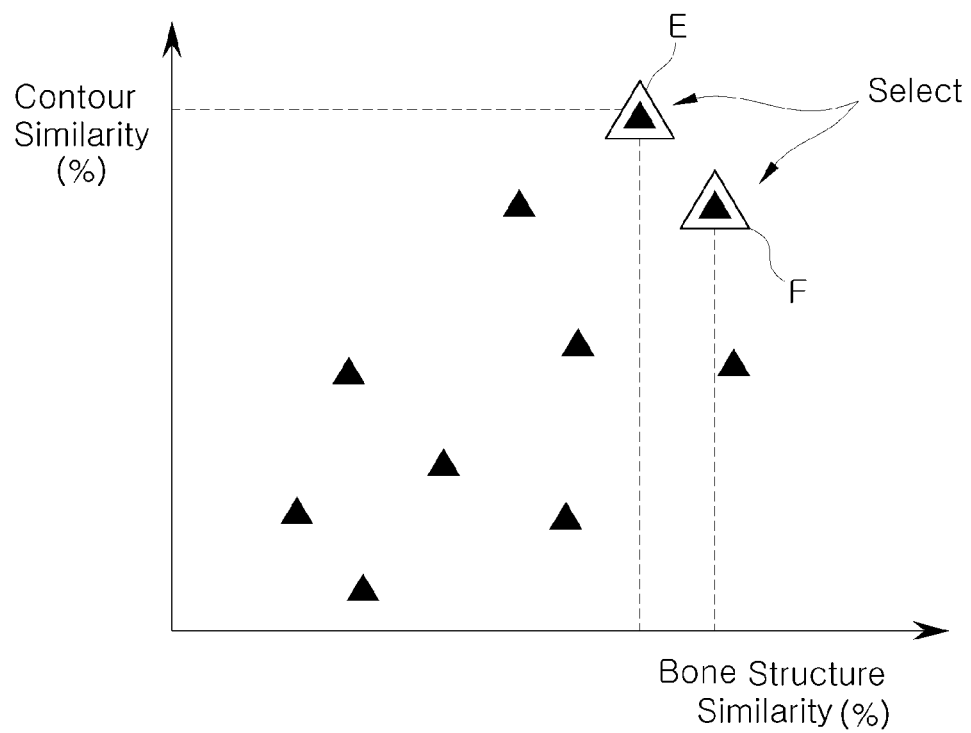

FIGS. 14, 15, and 16 are conceptual views for describing operation of comparing image data for the shape of an object, acquired through a scout scan according to an embodiment of the present disclosure, to pre-stored image data to select at least one image data having greater similarity than predetermined similarity.

The image processor 150 can compare image data for the shape of the object 30, acquired based on a scout scan image obtained by performing a scout scan on the top and lateral views of the object 30, to a plurality of image data stored in advance in the storage unit 145. According to the result of the comparison, the image processor 150 may select at least one image data having greater similarity than predetermined similarity to the image data acquired through the scout scan, from among the plurality of image data stored in advance in the storage unit 145.

The image processor 150 can compare projection profile data, bone structure image data, and contour image data for the top and lateral views of the object 30 to data stored in advance in the storage unit 145, as described above with reference to FIGS. 11A to 13B.

Factors which the image processor 150 uses as criteria for comparing data acquired through a scout scan to data stored in the storage unit 145 to determine similarity between the data may be two or all of projection profile data, bone structure image data, and contour image data.

Referring to FIG. 14, the image processor 150 can use projection profile data and bone structure image data as criteria for comparison to determine similarity between data acquired through a scout scan and data stored in the storage unit 145.

That is, the image processor 150 can compare projection profile data G1 and G2 of the object 30 acquired through a scout scan to projection profile data stored in advance in the storage unit 145, as described above with reference to FIGS. 11A and 11B. Also, the image processor 150 can compare bone structure image data R3 and R4 of the object 30 acquired through a scout scan, to bone structure image data stored in advance in the storage unit 145, as described above with reference to FIGS. 12A and 12B.

According to the result of the comparison, the image processor 150 may decide data having greater similarity than predetermined similarity, as data A and data B, with respect to similarity between projection profile data G1 and G2 of the object 30, acquired through a scout scan, and pre-stored projection profile data. That is, the data A and the data B among the plurality of pre-stored data can correspond to data that is most similar to the projection profile data G1 and G2 of the object 30, acquired through the scout scan.

Also, the image processor 150 can decide data having greater similarity than predetermined similarity, as data A and data B, with respect to similarity between bone structure image data R3 and R4 of the object 30, acquired through a scout scan, and pre-stored bone structure image data. Likewise, the data A and the data B among the plurality of pre-stored data can correspond to data that is most similar to the bone structure image data R3 and R4 of the object 30, acquired through the scout scan.

Referring to FIG. 15, the image processor 150 can use projection profile data and contour image data as criteria for comparison to determine similarity between data acquired through a scout scan and data stored in advance in the storage unit 145.

That is, the image processor 150 may compare projection profile data G1 and G2 of the object 30, acquired through a scout scan, to projection profile data stored in advance in the storage unit 145, as described above with reference to FIGS. 11A and 11B. Also, the image processor 150 can compare contour image data R5 and R6 of the object 30, acquired through a scout scan, to contour image data stored in advance in the storage unit 145, as described above with reference to FIGS. 13A and 13B.

According to the result of the comparison, the image processor 150 can decide data having greater similarity than predetermined similarity, as data C and data D, with respect to similarity between projection profile data G1 and G2 of the object 30, acquired through a scout scan, and pre-stored projection profile data. That is, the data C and the data D among the plurality of pre-stored data can correspond to data that is most similar to the projection profile data G1 and G2 of the object 30, acquired through the scout scan.

Also, the image processor 150 can decide data having greater similarity than predetermined similarity, as data C and data D, with respect to similarity between contour image data R5 and R6 of the object 30, acquired through a scout scan, and pre-stored contour image data. Likewise, the data C and the data D among the plurality of pre-stored data may correspond to data that is most similar to the contour image data R5 and R6 of the object 30, acquired through the scout scan.

The reason why data most similar to the projection profile data G1 and G2 of the object 30 acquired through the scout scan are decided as different data of data A and B and data C and D is because reference factors for determining similarity are projection profile data and bone structure image data in the case of FIG. 14, and are projection profile data and contour image data in the case of FIG. 15, and similarity is determined in consideration of the reference factors.

Referring to FIG. 16, the image processor 150 can use bone structure image data and contour image data as criteria for comparison to determine similarity between data acquired through a scout scan and data stored in advance in the storage unit 145.

That is, the image processor 150 can compare bone structure image data R3 and R4 of the object 30, acquired through a scout scan, to bone structure image data stored in advance in the storage unit 145, as described above with reference to FIGS. 12A and 12B. Also, the image processor 150 can compare contour image data R3 and R4 of the object 30 acquired through a scout scan, to contour image data stored in advance in the storage unit 145, as shown in FIGS. 13A and 13B.

According to the result of the comparison, the image processor 150 can decide data having greater similarity than predetermined similarity, as data E and data F, with respect to similarity between bone structure image data R3 and R4 of the object 30, acquired through a scout scan, and pre-stored bone structure image data. That is, the data E and the data F among the plurality of pre-stored data can correspond to data that is most similar to the bone structure image data R3 and R4 of the object 30, acquired through the scout scan.

Also, the image processor 150 can decide data having greater similarity than predetermined similarity, as data E and data F, with respect to similarity between contour image data R5 and R6 of the object 30, acquired through a scout scan, and pre-stored contour image data. Likewise, the data E and the data F among the plurality of pre-stored data can correspond to data that is most similar to the contour image data R5 and R6 of the object 30, acquired through the scout scan.

Figure 17:
FIG. 17 illustrates a table for describing operation of calculating a dose of radiation required for performing a CT scan on an object based on a dose of radiation corresponding to image data decided by an image processor, according to an embodiment of the present disclosure.

FIG. 17 is a table for describing operation of calculating a dose of radiation required for performing a CT scan on an object based on a dose of radiation corresponding to image data decided by an image processor, according to an embodiment of the present disclosure.

The data A and B decided based on projection profile data and bone structure image, as described above with reference to FIG. 14, can correspond to data that is most similar to image data of the object 30 acquired through a scout scan. That is, since information about the scout-scanned object 30 is most similar to information about an object corresponding to the data A and data B, a dose of radiation set to be applied to the case of performing a CT scan on the object corresponding to the data A and data B can be applied when a CT scan is performed on the scout-scanned object 30.

Accordingly, the controller 130 calculates an appropriate dose of radiation for performing a CT scan on the object 30, based on doses of radiation decided to respectively correspond to the data A and the data B.

Referring to FIG. 17, the data A decided by the image processor 150 may have similarity of 70% to projection profile data of the object 30 acquired through the scout scan, and the data B may have similarity of 90% to the projection profile data of the object 30. Also, the data A decided by the image processor 150 may have similarity of 85% to bone structure image data of the object 30 acquired through the scout scan, and the data B may have similarity of 80% to the bone structure image data of the scout-scanned object 30. Accordingly, the data A may have total similarity of 77.5% to the object 30, and the data B may have total similarity of 85% to the scout-scanned object 30.

As shown in FIG. 17, a dose of radiation corresponding to the data A is 200, and a dose of radiation corresponding to the data B is 170. This means that an appropriate dose of radiation required for performing a CT scan on an object corresponding to the data A is 200, and an appropriate dose of radiation required for performing a CT scan on an object corresponding to the data B is 170.

Therefore, the controller 130 assigns weight values to total similarities % of the data A and data B, and then calculates an appropriate dose of radiation required for performing a CT scan on the scout-scanned object 30, using radiation dose data corresponding to the resultant total similarities.

Figure 18:
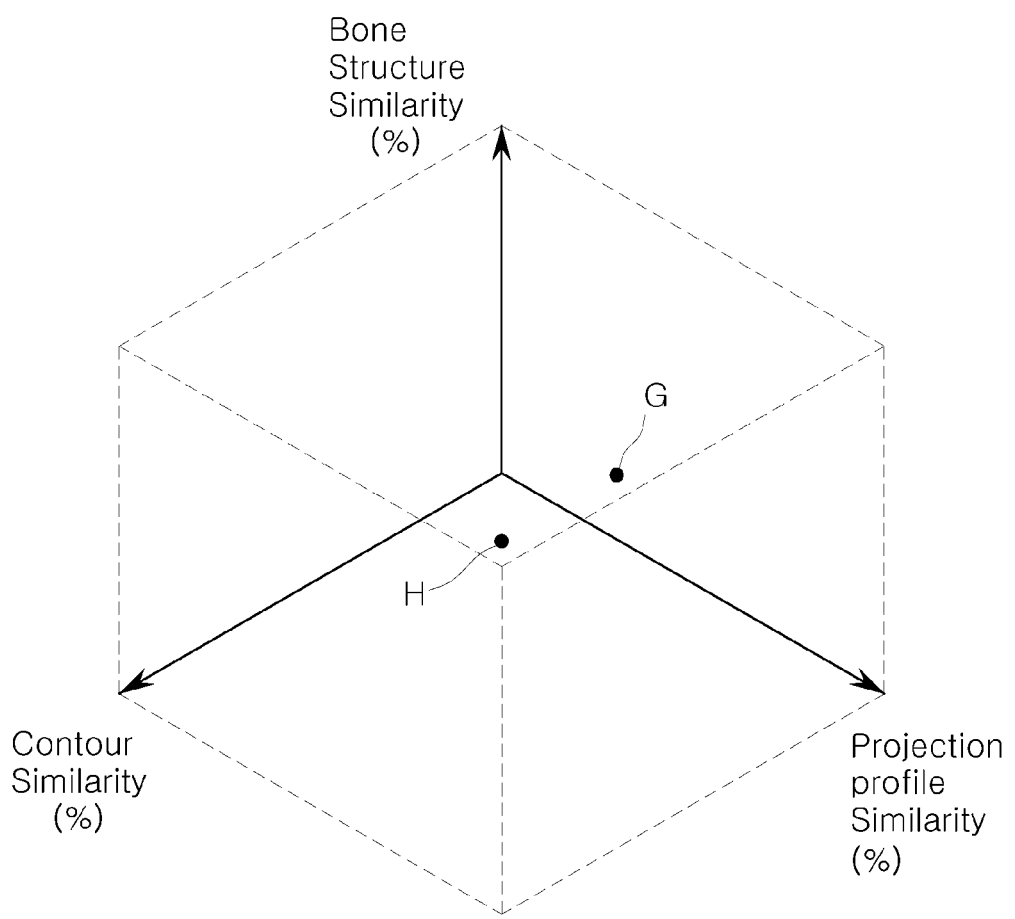
FIG. 18 illustrates a conceptual view for describing operation of comparing image data for the shape of an object acquired through a scout scan to pre-stored image data to select at least one image data having greater similarity than predetermined similarity, according to another embodiment of the present disclosure.

FIG. 18 is a conceptual view for describing operation of comparing image data for the shape of an object acquired through a scout scan to pre-stored image data to select at least one image data having greater similarity than predetermined similarity, according to another embodiment of the present disclosure.

FIG. 18 shows, unlike the cases of FIGS. 14, 15, and 16, a case in which criteria which the image processor 150 uses to compare data acquired through a scout scan to data stored in the storage unit 145 are all of projection profile data, bone structure image data, and contour image data.

Referring to FIG. 18, the image processor 150 can determine similarity between data acquired through a scout scan and data stored in advance in the storage unit 145, using projection profile data, bone structure image data, and contour image data as criteria for comparison. According to the result of the comparison, the image processor 150 can decide data having greater similarity than predetermined similarity, as data G and data H, with respect to similarity between projection profile data G1 and G2, bone structure image data R3 and R4, and contour image data R5 and R6 of the object 30, acquired through a scout scan, and pre-stored projection profile data, pre-stored bone structure image data, and pre-stored contour image data. The data G and data H among the plurality of pre-stored data may correspond to data most similar to projection profile data G1 and G2, bone structure image data R3 and R4, and contour image data R5 and R6 of the object 30, acquired through a scout scan.

Figure 19A:
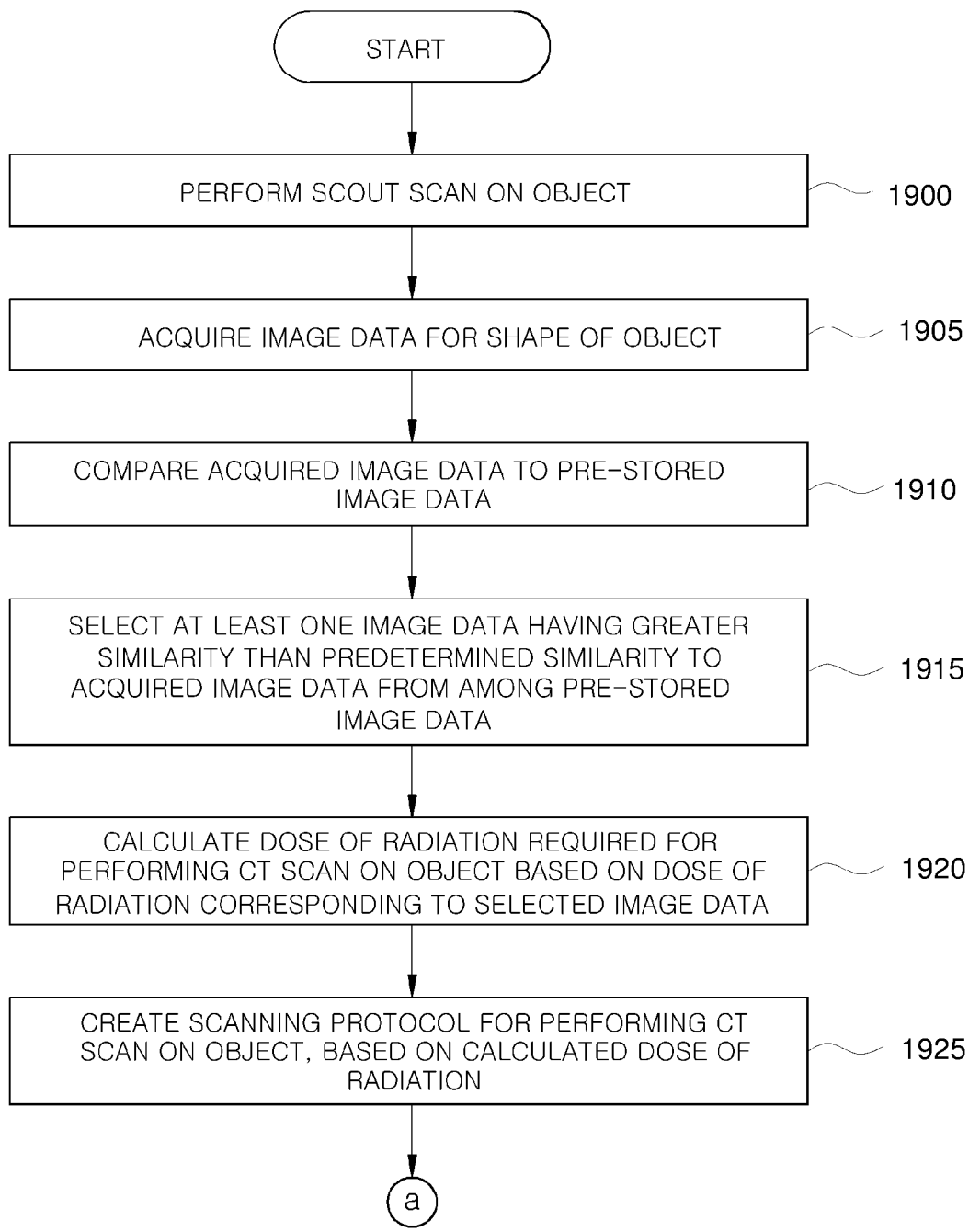
FIGS. 19A and 19B are flowcharts illustrating a method of controlling a CT apparatus, according to an embodiment of the present disclosure.
Figure 19B:
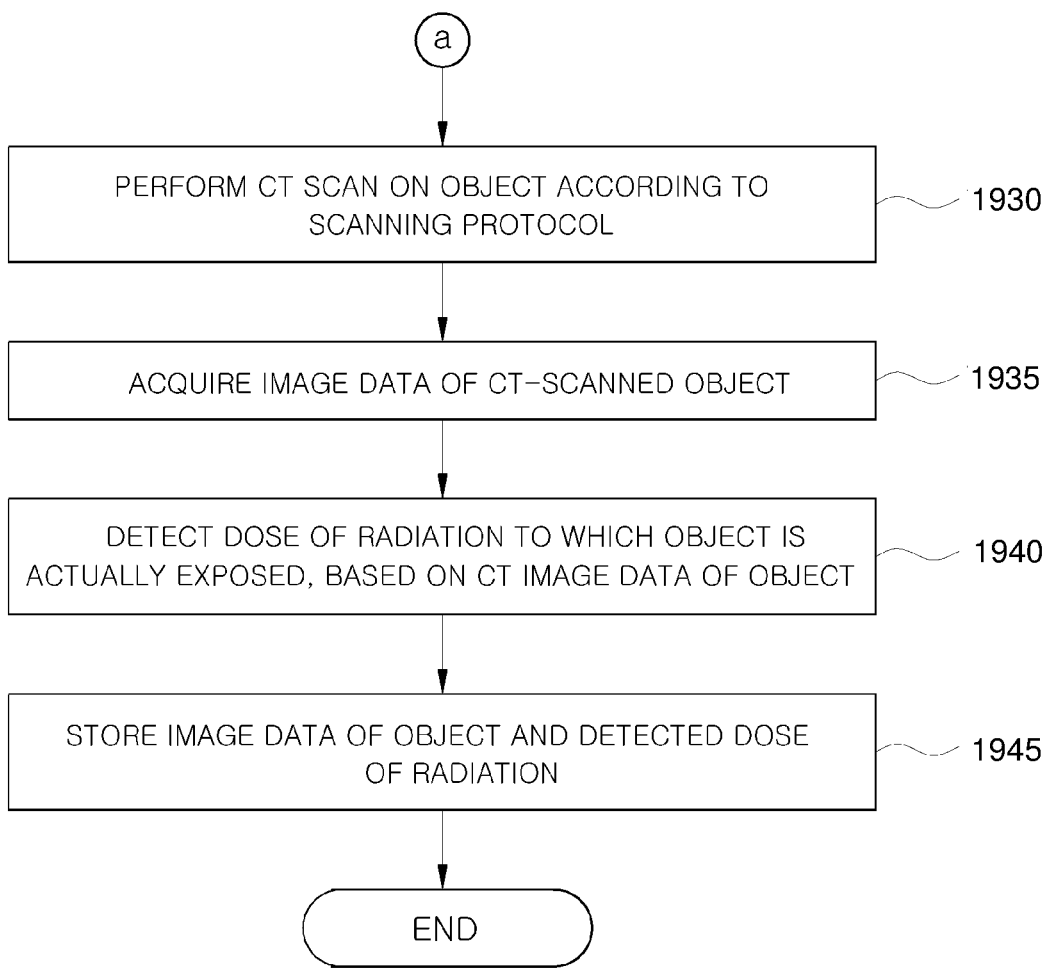

FIGS. 19A and 19B are a flowchart illustrating a method of controlling a CT apparatus, according to an embodiment of the present disclosure.

Referring to FIGS. 19A and 19B, if a scout scan is performed on the object 30, in operation 1900, the image processor 150 may acquire image data for the shape of the object 30, in operation 1905.

Since the scout scan for the object 30 is performed on top and lateral views of the object 30, the image processor 150 can acquire image data for each of the top and lateral views of the object 30.

Also, the image processor 150 can acquire at least one of projection profile data, bone structure image data, and contour image data, with respect to each of the top and lateral views of the object 30.

The projection profile data of the object 30 can be acquired based on at least one of the brightness and the intensity of image signals of a scout scan image of the object 30. The image processor 150 can perform image processing on the projection profile data to create at least one of bone structure image data and contour image data of the object 30.

The image processor 150 can compare the acquired image data of the object 30 to image data stored in advance in the storage unit 145, in operation 1910, and select at least one image data having greater similarity than predetermined similarity to the acquired image data from among the pre-stored image data, in operation 1915.

The controller 130 can calculate an appropriate dose of radiation required for performing a CT scan on the scout-scanned object 30, based on a dose of radiation corresponding to the image data decided by the image processor 150, in operation 1920. Also, the controller 130 can create a scanning protocol for performing a CT scan on the object 30, based on the calculated dose of radiation, in operation 1925. That is, the controller 130 can decide an appropriate dose of radiation required for performing a CT scan on the scout-scanned object 30, a position of the object 30 at which the CT scan is to be performed, and a scanning range of the object 30 on which the CT scan is to be performed, and also, the controller 130 can set a scanning protocol for parameter values, such as a tube voltage kV, tube current mAs, an exposure time, the kind and thickness of the filter, a target material of the anode, a focal spot size, etc., which are to be applied to the X-ray source 110.

Thereafter, according to the scanning protocol set under the control of the controller 130, a CT scan can be performed on the object 30, in operation 1930, and the image processor 150 can acquire image data of the CT-scanned object 30, in operation 1935.

Also, after the CT scan is performed on the object 30, the controller 130 can detect a dose of radiation to which the object 30 is actually exposed, based on CT image data of the object 30, acquired by the image processor 150, in operation 1940, and store the image data of the object 30 acquired through the CT scan and the detected dose of radiation in the storage unit 145 or the external server 500, in operation 1945, to be used as data for calculating an appropriate dose of radiation for the object 30.

Data about the image data of the object 30, acquired through the CT scan, a predicted value for a dose of radiation to which the object 30 is actually exposed when the CT scan is performed on the object 30, and data about a dose of radiation to which the object 30 is exposed, detected through the CT scan can be stored in the storage unit 145 or the external server 500 and updated in real time. That is, in order to calculate a dose of radiation to which the object 30 is expected to be exposed before a CT scan is performed on the object 30, previously acquired and calculated data about a dose of radiation can be stored, and a predicted value for a dose of radiation can be calculated based on the stored data, thereby increasing accuracy and reliability.

According to the CT apparatus and the control method thereof as described above, it is possible to accurately predict a dose of radiation including scattered radiation, which is applied when a CT scan is performed on an object, based on image data acquired through a scout scan. Also, by updating image data of an object acquired through a CT scan in database, it is possible to increase accuracy in predicting a dose of radiation, and by providing a CT scan with a low dose of radiation, it is possible to improve the quality of diagnosis and treatment through a CT scan.

The CT apparatus and the control method thereof according to the preferred embodiments of the present disclosure have been described with reference to the accompanying drawings. However, examples of the CT apparatus and the control method are not limited to the above-described embodiments, and the above-described embodiments are only exemplary in all aspects.

Although a few embodiments of the present disclosure have been shown and described, it would be appreciated by those skilled in the art that changes may be made in these embodiments without departing from the principles and spirit of the disclosure, the scope of which is defined in the claims and their equivalents.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A Computed Tomography (CT) apparatus for performing a CT scan on an object, comprising:
   a scanner configured to perform a scout scan on the object;
   storage configured to store patients' image data and a dose of radiation corresponding to each of the patients' image data;
   a processor configured to acquire image data for a shape of the object based on a scout scan image acquired by the scout scan, to compare the acquired image data to the image data stored in storage, and to select at least one image data having greater similarity than predetermined similarity to the acquired image data from among the image data stored in storage and
   calculate a dose of radiation to which the object is expected to be exposed, based on the dose of radiation corresponding to the selected at least one image data stored in the storage, and to perform a CT scan on the object based on the calculated dose of radiation, wherein the processor is further configured to acquire image data obtained by performing the CT scan on the object, and detect a dose of radiation to which the object is exposed, based on the image data obtained by performing the CT scan on the object, and the storage is further configured to update the patients' image data and the dose of radiation corresponding to each of the patients' image data by storing the detected dose of radiation to which the object is exposed and the image data obtained by performing the CT scan on the object.

2. The CT apparatus according to claim 1, wherein the scanner performs a scout scan on at least one of a top view of the object and a lateral view of the object.

3. The CT apparatus according to claim 1, wherein the image data for the shape of the object includes at least one image data between image data for a top view of the object and image data for a lateral view of the object.

4. The CT apparatus according to claim 1, wherein the image data for the shape of the object includes at least one image data among projection profile data of the object, bone structure image data of the object, and contour image data of the object.

5. The CT apparatus according to claim 4, wherein the processor acquires the projection profile data of the object, based on at least one of a brightness of the scout scan image and an intensity of image signals of the scout scan image.

6. The CT apparatus according to claim 4, wherein the processor performs image processing on the projection profile data of the object to create at least one image data between the bone structure image data of the object and the contour image data of the object.

7. The CT apparatus according to claim 4, wherein the processor compares the projection profile data of the object to projection profile data of the image data stored in the storage.

8. The CT apparatus according to claim 4, wherein the processor compares the bone structure image data of the object to bone structure image data of the image data stored in the storage.

9. The CT apparatus according to claim 4, wherein the processor compares the contour image data of the object to contour image data of the image data stored in the storage.

10. The CT apparatus according to claim 1, wherein the processor further compares the detected dose of radiation to which the object is exposed, to the dose of radiation to which the object is expected to be exposed to calculate a difference, and corrects the difference to perform a CT scan on the object.

11. A method for controlling a CT apparatus comprising a storage configured to store patients' image data and a dose of radiation corresponding to each of the patients' image data, comprising:

performing a scout scan on an object;

acquiring image data for a shape of the object based on a scout scan image obtained by performing the scout scan on the object;

comparing the acquired image data to the image data stored in storage;

selecting at least one image data having greater similarity than predetermined similarity to the acquired image data from among the image data stored in storage;

calculating a dose of radiation to which the object is expected to be exposed, based on the dose of radiation corresponding to the selected at least one image data stored in the storage;

performing a CT scan on the object based on the calculated dose of radiation;

acquiring image data obtained by performing the CT scan on the object;

detecting a dose of radiation to which the object is exposed based on the image data obtained by performing the CT scan on the object; and updating the patients' image data and the dose of radiation corresponding to each of the patients' image data by storing the detected dose of radiation to which the object is exposed and the image data obtained by performing the CT scan on the object.

12. The method according to claim 11, wherein the performing of the scout scan on the object comprises performing a scout scan on at least one of a top view of the object and a lateral view of the object.

13. The method according to claim 11, wherein the acquiring of the image data for the shape of the object comprises acquiring at least one data among projection profile data of the object, bone structure image data of the object, and contour image data of the object.

14. The method according to claim 13, wherein the acquiring of the image data for the shape of the object comprises acquiring the projection profile data of the object, based on at least one of a brightness of the scout scan image and an intensity of image signals of the scout scan image.

15. The method according to claim 13, wherein the acquiring of the image data for the shape of the object comprises performing image processing on the projection profile data of the object to create at least one data between the bone structure image data of the object and the contour image data of the object.

16. The method according to claim 13, wherein the comparing of the acquired image data to the image data stored in storage comprises comparing the acquired projection profile data of the object to projection profile data of the image data stored in the storage.

17. The method according to claim 13, wherein the comparing of the acquired image data to the image data stored in storage comprises comparing the acquired bone structure image data of the object to bone structure image data of the image data stored in the storage.

18. The method according to claim 13, wherein the comparing of the acquired image data to the image data stored in storage comprises comparing the acquired contour image data of the object to contour image data of the image data stored in the storage.

* * * * *